(12) United States Patent
Kanamori et al.

(10) Patent No.: US 10,097,744 B2
(45) Date of Patent: Oct. 9, 2018

(54) IMAGE FORMING APPARATUS

(71) Applicant: Panasonic Intellectual Property Management Co., Ltd., Osaka (JP)

(72) Inventors: Katsuhiro Kanamori, Nara (JP); Jun Ozawa, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 15/795,481

(22) Filed: Oct. 27, 2017

(65) Prior Publication Data

US 2018/0139365 A1 May 17, 2018

(30) Foreign Application Priority Data

Nov. 15, 2016 (JP) .................................. 2016-222604

(51) Int. Cl.
*G01J 4/00* (2006.01)
*H04N 5/225* (2006.01)
(Continued)

(52) U.S. Cl.
CPC ......... *H04N 5/2256* (2013.01); *G02B 27/283* (2013.01); *H04N 5/2254* (2013.01);
(Continued)

(58) Field of Classification Search
CPC ................ G01N 21/211; G01N 21/21; G01N 2021/213; G01J 4/00; G01B 11/0641
(Continued)

(56) References Cited

U.S. PATENT DOCUMENTS 5,738,429 A * 4/1998 Tagawa ................ G03B 21/132
353/122
9,645,074 B2 * 5/2017 Kanamori .............. G01N 21/21
(Continued)

FOREIGN PATENT DOCUMENTS

JP 9-127012 5/1997
JP 2011-150689 8/2011
(Continued)

OTHER PUBLICATIONS

Ji Qi et al., "Narrow band 3×3 Mueller polarimetric endoscopy", Biomedical Optics Express, vol. 4, No. 11, Oct. 2013, pp. 2433-2449.
(Continued)

*Primary Examiner* — Md M Rahman
(74) *Attorney, Agent, or Firm* — Wenderoth, Lind & Ponack, L.L.P.

(57) ABSTRACT

An image forming apparatus includes an illumination device, a beam splitter, an imaging device, and an image forming circuit. The illumination device includes first emitters emitting first light polarized at 30°, second emitters emitting second light polarized at 90°, and third emitters emitting third light polarized at 150°, and illuminates a subject with the first, second, and/or third light. The beam splitter splits returning light and outputs a first component polarized at 0°, a second component polarized at 60°, and a third component polarized at 120°. The imaging device has an imaging surface that includes a first region receiving the first component, a second region receiving the second component, and a third region receiving the third component. The image forming circuit generates an image of the subject based on first, second, and third groups of images acquired when the subject is illuminated with the first, second, and third light.

8 Claims, 19 Drawing Sheets

(51) Int. Cl.
*H04N 5/345* (2011.01)
*G02B 27/28* (2006.01)
*H04N 5/235* (2006.01)

(52) U.S. Cl.
CPC .......... *H04N 5/2354* (2013.01); *H04N 5/345* (2013.01); *H04N 2005/2255* (2013.01)

(58) Field of Classification Search
USPC ....................................................... 356/369
See application file for complete search history.

(56) References Cited

U.S. PATENT DOCUMENTS

2012/0242835 A1   9/2012   Li et al.
2015/0219552 A1   8/2015   Kanamori
2016/0275362 A1   9/2016   Aoki et al.

FOREIGN PATENT DOCUMENTS

JP   2012-045029   3/2012
JP   2015-164518   9/2015
JP   2016-177686   10/2016

OTHER PUBLICATIONS

Daisuke Miyazaki et al., "Measurement of Surface Shape of Transparent Objects Based on Polarization and Geometrical Analysis", Proceedings of the Meeting on Image Recognition and Understanding (MIRU2002), Jul. 2002, pp. 263-268 (English Abstract).

Gary A. Atkinson et al., "Recovery of surface orientation from diffuse polarization", IEEE Transactions on Image Processing, vol. 15, No. 6, Mar. 2006, pp. 1653-1664.

Katsuhiro Kanamori, "Image enhancement of surface microstructure on mucosa for polarimetric endoscopy", Proc. of SPIE vol. 9318, Mar. 2015, 93180O-1 to 93180O-14.

\* cited by examiner $\theta_p$

IMAGE FORMING APPARATUS

BACKGROUND

1. Technical Field

The present disclosure relates to image forming apparatuses.

2. Description of the Related Art

Looking into the polarization state of a light beam from a subject makes it possible to obtain information on the subject that cannot be obtained through a typical observation based on the luminance, and various studies are being conducted on the application of polarization. For example, Japanese Unexamined Patent Application Publication No. 2015-164518 and Katsuhiro Kanamori, "Image enhancement of surface micro-structure on mucosa for polarimetric endoscopy," Proc. of SPIE, 2015, Vol. 9318, 93180O-1 to 93180O-14 propose the use of polarization imaging for observing the surface microstructures of tissue covered with a semi-transparent mucous. According to the techniques described in Japanese Unexamined Patent Application Publication No. 2015-164518 and in Kanamori, a pair of parallel-Nicols images and another pair of crossed-Nicols images are acquired with an illumination light beam of which the polarization plane of a linearly polarized light beam is varied by 90° between the images in each pair, and an image obtained by averaging the two parallel-Nicols images and an image obtained by averaging the two crossed-Nicols images are subjected to subtraction processing. According to Japanese Unexamined Patent Application Publication No. 2015-164518 and Kanamori, an image in which fine concavities and convexities in the surface of the subject are enhanced can be obtained. For reference, the entire content disclosed in each of Japanese Unexamined Patent Application Publication No. 2015-164518 and Kanamori is incorporated herein.

Japanese Unexamined Patent Application Publication No. 2012-045029 discloses an endoscopic diagnosis apparatus configured to be capable of acquiring Mueller matrix information of a subject. The Mueller matrix is a 4×4 matrix that describes an effect that an optical element has on the polarization state. Ji Qi, Menglong Ye, Mohan Singh, Neil T. Clancy, and Daniel S. Elson, "Narrow band 3×3 Mueller polarimetric endoscopy," Biomedical Optics Express, 1 November, 2013, Vol. 4, No. 11, 2433-2449 discusses the feasibility of applying, to an endoscopic diagnosis, a Mueller matrix of which the number of matrix elements is reduced to 3×3 with an attention given to a linear polarization component.

In addition, a technique in which a subject is irradiated with an unpolarized light beam and the shape of the subject is estimated on the basis of the degree of polarization of a reflection light beam from the subject is being proposed. Daisuke Miyazaki and Katsushi Ikeuchi "Measurement of Surface Shape of Transparent Objects Based on Polarization and Geometrical Analysis," Meeting on Image Recognition and Understanding (held in Aichi from Jul. 30 to Aug. 1, 2002) Proceedings II, pp. 263-268 proposes a method in which a transparent object is irradiated with an unpolarized light beam, the direction normal to the surface of the transparent object is obtained from the degree of polarization of a reflection light beam, and the surface shape of the transparent is measured. Gary A. Atkinson and Edwin R. Hancock, "Recovery of surface orientation from diffuse polarization," IEEE TRANSACTIONS ON IMAGE PROCESSING, JUNE, 2006, VOL. 15, NO. 6, pp. 1653-1664 measures the surface shape of a porcelain object by using the degree of polarization of a reflection light beam.

SUMMARY

One non-limiting and exemplary embodiment provides an image forming apparatus having a novel configuration.

In one general aspect, the techniques disclosed here feature an image forming apparatus. The image forming apparatus includes an illumination device that includes one or more first emitters, one or more second emitters, and one or more third emitters, the one or more first emitters each emitting a first light beam having a polarization direction of 30°, the one or more second emitters each emitting a second light beam having a polarization direction of 90°, the one or more third emitters each emitting a third light beam having a polarization direction of 150°, the illumination device illuminating a subject with at least one of the first, second, and third light beams; a beam splitter that splits a returning light beam from the subject and outputs a first component having a polarization direction of 0°, a second component having a polarization direction of 60°, and a third component having a polarization direction of 120°; an imaging device having an imaging surface that includes a first region that receives the first component, a second region that receives the second component, and a third region that receives the third component; and an image forming circuit, wherein the image forming circuit generates an image of the subject on the basis of a first group of images of the first component, the second component, and the third component acquired by the imaging device when the subject is illuminated with the first light beam among the first, second, and third light beams, a second group of images of the first component, the second component, and the third component acquired by the imaging device when the subject is illuminated with the second light beam among the first, second, and third light beams, and a third group of images of the first component, the second component, and the third component acquired by the imaging device when the subject is illuminated with the third light beam among the first, second, and third light beams.

It is to be noted that general or specific embodiments of the above may be implemented in the form of a system, a method, an integrated circuit, a computer program, or a computer-readable recording medium, or through any desired combination of an apparatus, a system, a method, an integrated circuit, a computer program, and a computer-readable recording medium. Examples of a computer-readable recording medium include a nonvolatile recording medium, such as a Compact Disc-Read Only Memory (CD-ROM).

According to the present disclosure, an image forming apparatus having a novel configuration is provided. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
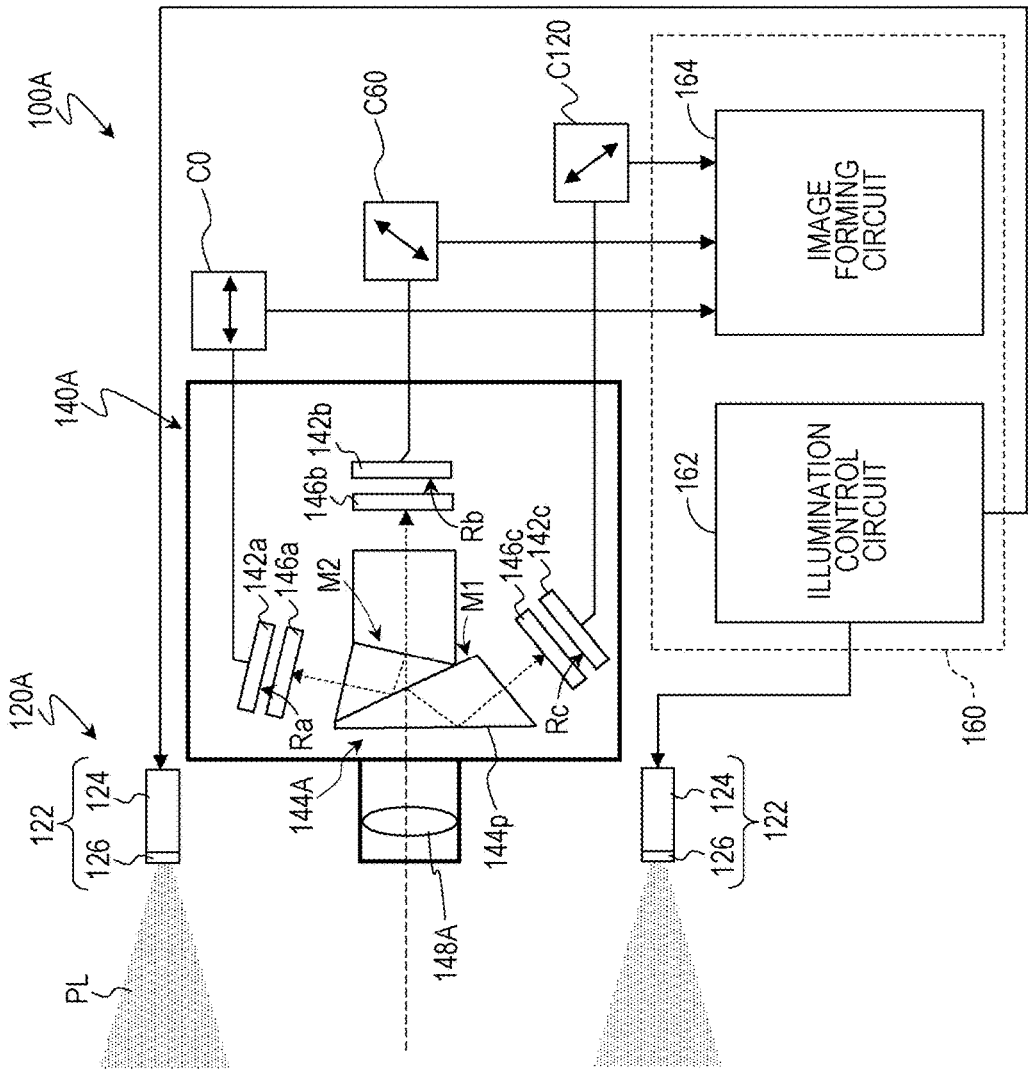
FIG. 1 illustrates an exemplary configuration of an image forming apparatus according to a first embodiment of the present disclosure.

The overview of one aspect of the present disclosure are as follows.

Item 1

An image forming apparatus, comprising:

an illumination device including one or more first emitters, one or more second emitters, and one or more third emitters, the one or more first emitters each emitting a first light beam having a polarization direction of 30°, the one or more second emitters each emitting a second light beam having a polarization direction of 90°, the one or more third emitters each emitting a third light beam having a polarization direction of 150°, the illumination device illuminating a subject with at least one of the first, second, and third light beams;

a beam splitter that splits a returning light beam from the subject and outputs a first component having a polarization direction of 0°, a second component having a polarization direction of 60°, and a third component having a polarization direction of 120°;

an imaging device having an imaging surface that includes a first region that receives the first component, a second region that receives the second component, and a third region that receives the third component; and an image forming circuit, wherein the image forming circuit generates an image of the subject on the basis of a first group of images of the first component, the second component, and the third component acquired by the imaging device when the subject is illuminated with the first light beam among the first, second, and third light beams, a second group of images of the first component, the second component, and the third component acquired by the imaging device when the subject is illuminated with the second light beam among the first, second, and third light beams, and a third group of images of the first component, the second component, and the third component acquired by the imaging device when the subject is illuminated with the third light beam among the first, second, and third light beams.

Item 2

In the image forming apparatus according to Item 1, the beam splitter includes a prism, and first, second, and third analyzers of which directions of transmission axes are 0°, 60°, and 120°, respectively.

Item 3

An image forming apparatus, comprising:

an illumination device including one or more first emitters, one or more second emitters, and one or more third emitters, the one or more first emitters each emitting a first light beam having a polarization direction of 30°, the one or more second emitters each emitting a second light beam having a polarization direction of 90°, the one or more third emitters each emitting a third light beam having a polarization direction of 150°, the illumination device illuminating a subject with at least one of the first, second, and third light beams;

an imaging device that includes a housing having first, second, and third apertures provided therein, and an image sensor having an imaging surface;

one or more objective lenses located between the subject and the imaging surface;

a first analyzer that is disposed at a position of the first aperture and of which a direction of a transmission axis is 0°;

a second analyzer that is disposed at a position of the second aperture and of which a direction of a transmission axis is 60°;

a third analyzer that is disposed at a position of the third aperture and of which a direction of a transmission axis is 120°; and an image forming circuit, wherein the imaging surface of the imaging device includes a first region, a second region, and a third region, the first region receiving a fourth light beam, of a returning light beam from the subject, that has passed through the first analyzer, the second region receiving a fifth light beam, of the returning light beam from the subject, that has passed through the second analyzer, the third region receiving a sixth light beam, of the returning light beam from the subject, that has passed through the third analyzer, and wherein the image forming circuit generates an image of the subject on the basis of a first group of images of the fourth, fifth, and sixth light beams acquired by the imaging device when the subject is illuminated with the first light beam among the first, second, and third light beams, a second group of images of the fourth, fifth, and sixth light beams acquired by the imaging device when the subject is illuminated with the second light beam among the first, second, and third light beams, and a third group of images of the fourth, fifth, and sixth light beams acquired by the imaging device when the subject is illuminated with the third light beam among the first, second, and third light beams.

Item 4

In the image forming apparatus according to Item 3, the one or more objective lenses include a first objective lens located in an optical path connecting the subject and the first region, a second objective lens located in an optical path connecting the subject and the second region, and a third objective lens located in an optical path connecting the subject and the third region.

Item 5

The image forming apparatus according to Item 3 further includes a microlens array located between the one or more objective lenses and the imaging surface, wherein the one or more objective lenses are a single objective lens that receives a light beam that has passed through the first aperture, a light beam that has passed through the second aperture, and a light beam that has passed through the third aperture.

Item 6

In the image forming apparatus according to any one of Items 1 to 5, the first group of images includes two first polarization images and one first crossed-Nicols image, the second group of images includes two second polarization images and one second crossed-Nicols image, the third group of images includes two third polarization images and one third crossed-Nicols image, and the image forming circuit forms an averaged pseudo-parallel-Nicols image that is based on the two first polarization images, the two second polarization images, and the two third polarization images and an averaged crossed-Nicols image that is based on the one first crossed-Nicols image, the one second crossed-Nicols image, and the one third crossed-Nicols image, and forms an image of the subject by obtaining a difference between the averaged pseudo-parallel-Nicols image and the averaged crossed-Nicols image.

Item 7

In the image forming apparatus according to any one of Items 1 to 6, the illumination device further illuminates the subject simultaneously with the first, second, and third light beams, and the imaging device images each of a light beam incident on the first region, a light beam incident on the second region, and a light beam incident on the third region when the subject is illuminated with the first, second, and third light beams.

Hereinafter, embodiments of the present disclosure will be described in detail with reference to the drawings. It is to be noted that the embodiments described hereinafter merely illustrate general or specific examples. The numerical values, the shapes, the materials, the constituent elements, the arrangement and the connection modes of the constituent elements, the steps, the order of the steps, and so forth indicated in the embodiments hereinafter are examples and are not intended to limit the present disclosure. Various aspects described in the present specification can be combined together unless any inconsistency arises. In addition, among the constituent elements described in the embodiments hereinafter, a constituent element that is not described in an independent claim indicating the broadest concept is described as an optional constituent element. In the following description, constituent elements having substantially identical functions are given identical reference characters, and descriptions thereof will be omitted in some cases.

First Embodiment

FIG. 1 illustrates an exemplary configuration of an image forming apparatus according to a first embodiment of the present disclosure. An image forming apparatus 100A illustrated in FIG. 1 generally includes an illumination device 120A that includes a plurality of emitters 122, a beam splitter 144A, an imaging device 140A, and a control circuit 160. The illumination device 120A irradiates a subject with a linearly polarized light beam or an unpolarized light beam, and the imaging device 140A captures an image of the subject irradiated with the linearly polarized light beam or the unpolarized light beam. In the configuration illustrated in FIG. 1, the control circuit 160 includes an illumination control circuit 162 and an image forming circuit 164.

Each of the plurality of emitters 122 includes a light source 124 and a polarizer 126 disposed in front of the light source 124. Each emitter 122 emits a linearly polarized light beam PL polarized in accordance with the direction of the transmission axis of a corresponding polarizer 126. The light source 124 can be constituted, for example, by a well-known light-emitting element, such as a white light-emitting diode or an infrared light-emitting diode, and the polarizer 126 can be constituted by a commercially available polarizing sheet, metal wire grid polarizer, or the like.

As will be described later in detail, the plurality of emitters 122 include three types of polarizers of which the directions of the transmission axes differ from one another by 60°. The illumination device 120A selectively turns on, among the plurality of light sources 124, the light sources 124 that are disposed behind the polarizers 126 of which the directions of the transmission axes coincide with one another and can thus irradiate the subject successively with linearly polarized light beams polarized in different directions. In addition, the illumination device 120A can irradiate the subject with an unpolarized light beam by turning on, for example, all of the plurality of light sources 124. In the present specification, the term "polarization direction" refers to a smaller one of the angles formed by a reference direction (e.g., horizontal direction) and the vibration direction of the electric field vector measured in the counter-clockwise direction as viewed in the direction from the subject toward the image forming apparatus. The plurality of emitters 122 can be driven on the basis of the control of the illumination control circuit 162.

The imaging device 140A includes an objective lens 148A and image sensors 142a, 142b, and 142c. The image sensors 142a to 142c can each be constituted by a CCD (charge-coupled device) image sensor, a CMOS (complementary metal-oxide semiconductor) image sensor, a so-called laminated image sensor in which an organic or inorganic photoelectric conversion layer is laminated on a semiconductor substrate, or the like.

In the configuration illustrated in FIG. 1, the beam splitter 144A is disposed at a position that is inside the imaging device 140A and at which a light beam that has passed through the objective lens 148A is incident on the beam splitter 144A. The beam splitter 144A typically includes one or more prisms 144p and forms three light beams from an incident light beam (a reflection light beam from the subject in this case). In this example, the beam splitter 144A has reflection surfaces M1 and M2 located between two adjacent prisms. As schematically illustrated in FIG. 1, a portion of the incident light beam is reflected at the reflection surface M1, is further reflected at an interface between the prism and the air, and emerges toward the image sensor 142c. A portion of the light beam that has been transmitted through the reflection surface M1 and has reached the reflection surface M2 is reflected at the reflection surface M2, is further reflected at the reflection surface M1, and emerges toward the image sensor 142a. The remaining portion of the light beam that has been transmitted through the reflection surface M1 is transmitted through the reflection surface M2 and emerges toward the image sensor 142b. The reflectance of the reflection surface M1 is set such that the reflection surface M1 reflects approximately one-third of the incident light beam, and the reflectance of the reflection surface M2 is set such that the reflection surface M2 reflects approximately one-half of the incident light beam. The reflection surfaces M1 and M2 may have a metal film or a dielectric multilayer film, for example.

The beam splitter 144A further includes an analyzer 146a located in an optical path connecting the subject and the image sensor 142a, an analyzer 146b located in an optical path connecting the subject and the image sensor 142b, and an analyzer 146c located in an optical path connecting the subject and the image sensor 142c. Similarly to the polarizers 126 in the emitters 122, the analyzers 146a, 146b, and 146c can each be constituted by a commercially available polarizing sheet, metal wire grid polarizer, or the like. A first light beam that emerges from the beam splitter 144A and is incident on the image sensor 142a is a linearly polarized light beam that has passed through the analyzer 146a. In a similar manner, a second light beam that emerges from the beam splitter 144A and is incident on the image sensor 142b is a linearly polarized light beam that has passed through the analyzer 146b, and a third light beam that emerges from the beam splitter 144A and is incident on the image sensor 142c is a linearly polarized light beam that has passed through the analyzer 146c.

The directions of the transmission axes of the analyzers 146a, 146b, and 146c differ from one another by 60°. The directions of the transmission axes of the analyzers 146a, 146b, and 146c are, for example, 0°, 60°, and 120°, respectively. Therefore, the beam splitter 144A splits a returning light beam from the subject into a first component having a polarization direction of 0°, a second component having a polarization direction of 60°, and a third component having a polarization direction of 120° and directs the first, second, and third components toward the image sensors 142a, 142b, and 142c, respectively.

The imaging surface of the image sensor 142a receives, of the returning light beam from the subject, a polarization component polarized at 0° (first component), and the image sensors 142b and 142c receive, of the returning light beam from the subject, a polarization component polarized at 60° (second component) and a polarization component polarized at 120° (third component), respectively. In other words, the imaging device 140A can acquire, at once, three images of the subject that are based on the different polarization components (hereinafter, each image may be referred to as a "polarization image") under the illumination light beam (linearly polarized light beam or unpolarized light beam) from the illumination device 120A. When the imaging surfaces of the image sensors 142a, 142b, and 142c are regarded as a single imaging surface as a whole, the configuration can be rephrased as follows: the imaging surface of the imaging device 140A includes a first region Ra that receives the first component, a second region Rb that receives the second component, and a third region Rc that receives the third component. In this example, the first region Ra, the second region Rb, and the third region Rc correspond to the imaging surfaces of the image sensors 142a, 142b, and 142c, respectively.

In this manner, the imaging device 140A acquires a polarization image C0 of a light beam having a polarization direction of 0°, a polarization image C60 of a light beam having a polarization direction of 60°, and a polarization image C120 of a light beam having a polarization direction of 120° in a single instance of imaging with the image sensor 142a, the image sensor 142b, and the image sensor 142c.

In FIG. 1, the thick double-headed arrows enclosed by the rectangles schematically representing the respective polarization images C0, C60, and C120 each indicate the vibration direction of the electric field vector of the light beam incident on the image sensor, or in other words, the polarization direction of the light beam forming the polarization image. The direction indicated by each thick double-headed arrow coincides with the direction of the transmission axis of a corresponding analyzer. Hereinafter, the polarization direction of a light beam forming a polarization image or the direction of the transmission axis of an analyzer may be indicated by a thick double-headed arrow in other drawings of the present disclosure.

In the present specification, the direction of the transmission axis of an analyzer is expressed by a smaller one of the angles formed by a reference direction (e.g., horizontal direction) and the direction parallel to the transmission axis of the analyzer measured in the counterclockwise direction as viewed toward the imaging surface. It is to be noted that the aforementioned angles of 0°, 60°, and 120° do not indicate the absolute directions of the transmission axes of the analyzers 146a, 146b, and 146c. It suffices that the relationship among the directions of the transmission axes of the analyzers 146a, 146b, and 146c be a predetermined relationship. In addition, these values of the angles are merely examples, and it is not necessary that the angle indicating the direction of the transmission axis of an analyzer precisely match a specific value illustrated in the present specification. For example, a deviation of several degrees is permissible. However, the smaller the deviation is, the more efficiently the light beam can be used.

In the configuration illustrated in FIG. 1, the control circuit 160 includes the illumination control circuit 162 that controls the operation of the illumination device 120A and the image forming circuit 164 that forms an image of the subject on the basis of a signal from the imaging device 140A. The control circuit 160 may, for example, be a microcontroller or the like having a central processing unit (CPU). The illumination control circuit 162 and the image forming circuit 164 may be a portion of a single microcontroller or may each be an independent processing circuit. For example, the image forming circuit 164 may be implemented by a digital signal processor (DSP), an application specific integrated circuit (ASIC), a field-programmable gate array (FPGA), or the like. The control circuit 160 may include one or more memories.

The image forming apparatus 100A is configured to be capable of selecting, for example, between a first mode in which the subject is irradiated with a linearly polarized light beam and imaged and a second mode in which the subject is irradiated with an unpolarized light beam and imaged. As will be described later in detail, in the first mode, the illumination control circuit 162 controls the illumination device 120A such that, of the plurality of light sources 124, the light sources 124 disposed behind the polarizers 126 of which the directions of the transmission axes coincide with one another are selectively turned on. In the first mode, the subject is irradiated by the illumination device 120A successively with linearly polarized light beams of which the angles of the polarization planes differ from one another by 60°. On the basis of the control of the control circuit 160, for example, the imaging device 140A executes imaging each time the subject is irradiated with a light beam having a different polarization plane in synchronization as the illumination device 120A switches the linearly polarized light beams. In other words, in the first mode, imaging is executed three times with the polarization state of the illumination light beam being varied. In this case, three polarization image C0, C60, and C120 are acquired simultaneously in each of the three instances of imaging. In other words, the total of nine polarization images are acquired in the first mode. The image forming circuit 164 forms an image of the subject on the basis of these nine polarization images. The first mode may be referred to as a surface observation mode.

Meanwhile, in the second mode, the illumination control circuit 162 typically controls the illumination device 120A such that all of the plurality of light sources 124 are turned on. As will be described later, in this case, the subject can be illuminated with a substantially unpolarized light beam. In the second mode as well, the imaging device 140A acquires three polarization images C0, C60, and C120. The data of the polarization images C0, C60, and C120 obtained at this time can be used to estimate the shape of the subject. The second mode may be referred to as a shape measuring mode. A switch between the first and second modes can be made on the basis of, for example, a user instruction through an input device (button, touch panel, etc.) (not illustrated). Alternatively, a switch between these modes may be made automatically on the basis of the control of the control circuit 160 in accordance with an instruction of a program stored in a memory. For example, the second mode may be executed automatically and continually upon the first mode having been executed. The order in which the first mode and the second mode are executed may be reversed.

According to a typical embodiment of the present disclosure, while the illumination optical system and the imaging optical system are shared, for example, polarization imaging that is advantageous in observing the fine concavities and convexities in the surface of the subject and that is carried out under the irradiation of a linearly polarized light beam and polarization imaging that provides information useful for estimating the shape of the subject and that is carried out under the irradiation of an unpolarized light beam can be switched therebetween and executed with a single apparatus.

Figure 2:
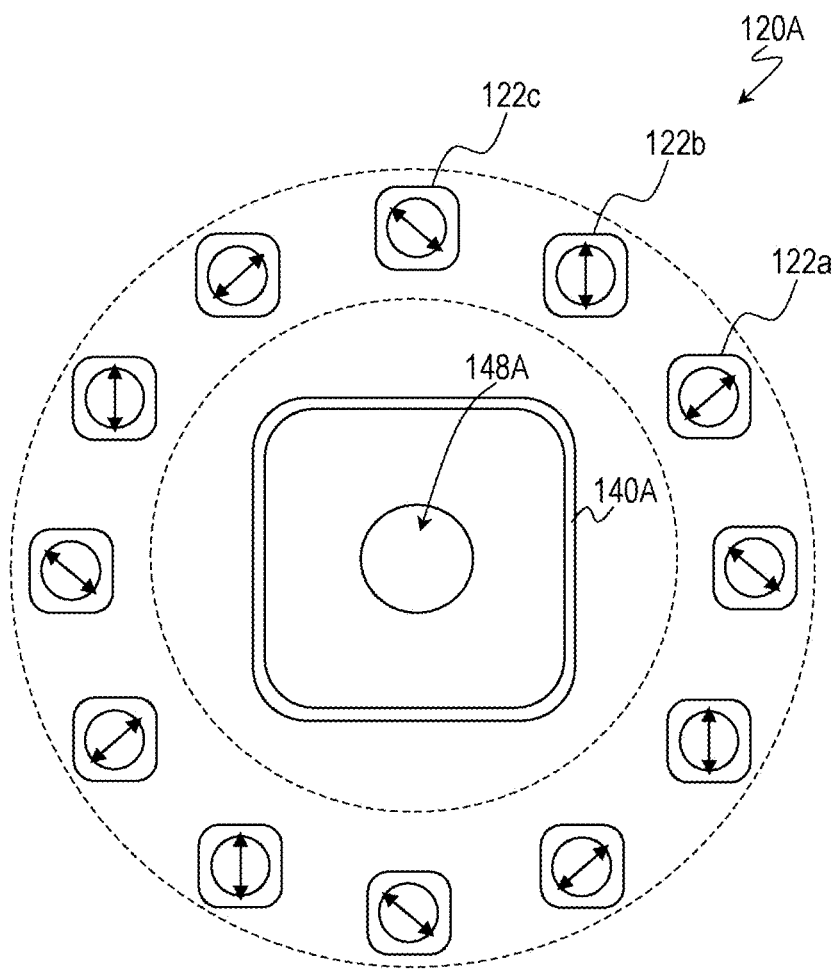
FIG. 2 illustrates a typical example of the arrangement of a plurality of emitters as viewed from a subject.

FIG. 2 illustrates a typical example of the arrangement of the plurality of emitters 122 as viewed from the subject. In the example illustrated in FIG. 2, the plurality of emitters 122 in the illumination device 120A include a plurality of emitters 122a, 122b, and 122c. Typically, the emitters 122a to 122c are disposed within the same plane, and the objective lens 148A of the imaging device 140A is located, for example, in the plane in which the emitters 122a to 122c are disposed. A plurality of first surfaces that are included in the plurality of emitters 122a and that emit light beams to the outside of the plurality of emitters 122a, a plurality of second surfaces that are included in the plurality of emitters 122b and that emit light beams to the outside of the plurality of emitters 122b, and a plurality of third surfaces that are included in the plurality of emitters 122c and that emit light beams to the outside of the plurality of emitters 122c may all be disposed in a first plane. In addition, the endmost surface of the objective lens 148A may lie in the same plane as the first plane.

FIG. 2 illustrates a typical arrangement of the emitters 122a to 122c as viewed from the subject along the direction normal to the plane in which the emitters 122a to 122c are disposed. In this example, the plurality of emitters 122 are disposed so as to surround the imaging device 140A as the illumination device 120A and the imaging device 140A are viewed from the subject. Although it is not essential that the plurality of emitters 122 surround the imaging device 140A, disposing the plurality of emitters 122 so as to surround the imaging device 140A is advantageous in terms of reducing the size of the apparatus. In addition, disposing the plurality of emitters 122 so as to surround the imaging device 140A makes it possible to achieve illumination close to coaxial illumination.

In this example, the illumination device 120A includes four each of the emitters 122a, 122b, and 122c, and the emitters 122a, 122b, and 122c are disposed in a ring-shape as indicated by the dashed double circle illustrated in FIG. 2. Herein, four sets of emitters 122a, 122b, and 122c are disposed in the counterclockwise direction along the circumference of a circle centered on the position of the objective lens 148A. In the configuration illustrated in FIG. 2, the centers of the respective emitters 122a, 122b, and 122c are located at the vertices of a right dodecagon.

In a typical embodiment of the present disclosure, the directions of the transmission axes of the polarizers 126 differ by 60° among the emitters 122a, 122b, and 122c. The direction of the transmission axis of the polarizer 126 in the emitter 122a is, for example, 30°, and the directions of the transmission axes of the polarizers 126 in the emitter 122b and the emitter 122c are, for example, 90° and 150°, respectively. Similarly to the angles indicating the directions of the transmission axes of the analyzers, it is not necessary that the angle indicating the direction of the transmission axis of a polarizer precisely match a specific value indicated in the present specification, and a deviation of several degrees, for example, is permissible. In the present specification, the direction of the transmission axis of a polarizer 126 is expressed by a smaller one of the angles formed by the aforementioned reference direction and the direction parallel to the transmission axis of the polarizer 126 measured in the counterclockwise direction as the light source 124 is viewed from the subject. In FIG. 2, the thick double-headed arrows indicated inside the circles illustrated at the positions of the emitters 122a, 122b, and 122c can be said to represent the polarization directions of the linearly polarized light beams with which the subject is irradiated. In other drawings of the present disclosure, the polarization direction of a linearly polarized light beam with which the subject is irradiated may be represented by a thick double-headed arrow illustrated inside a circle.

The feature that the directions of the transmission axes differ by 60° among the emitters 122a, 122b, and 122c can be said to be common to the relationship of the directions of the transmission axes of the analyzers 146a, 146b, and 146c. However, it should be noted that the directions of the transmission axes of the polarizers 126 in the emitters 122a, 122b, and 122c do not coincide with the directions of the transmission axes of the analyzers 146a, 146b, and 146c, respectively. For example, the direction of the transmission axis of the polarizer 126 in the emitter 122a is 30° herein, and the value of this angle differs by 30° from the value of the direction of the transmission axis of the analyzer 146a (0°) and from the value of the direction of the transmission axis of the analyzer 146b (60°).

According to the configuration of the illumination device 120A as illustrated in FIG. 2, the subject can be irradiated with a linearly polarized light beam having a polarization direction of 30° as, among the plurality of emitters 122, the emitters 122b and 122c are turned off and the emitters 122a are selectively turned on. The subject can be irradiated with a linearly polarized light beam having a polarization direction of 90° when the emitters 122b are selectively turned on, and the subject can be irradiated with a linearly polarized light beam having a polarization direction of 150° when the emitters 122c are selectively turned on. Alternatively, the subject can be irradiated with an unpolarized light beam when the emitters 122a, 122b, and 122c are turned on at once. As described above, since the directions of the transmission axes of the polarizers 126 differ by 60° among the emitters 122a, 122b, and 122c, linearly polarized light beams from the emitters 122a, 122b, and 122c can be mixed to uniformity, and a substantially unpolarized light beam can be obtained.

In the example illustrated in FIG. 2, for example, the four emitters 122a are disposed such that their respective centers are located on the circumference of a circle and are also disposed such that their respective centers are located on the vertices of a square. To rephrase, a square is drawn by connecting the positions of the four emitters 122a. In a similar manner, the four emitters 122b are disposed such that their respective centers are located on the vertices of a square centered on the position of the objective lens 148A, and the four emitters 122c are also disposed such that their respective centers are located on the vertices of a square centered on the position of the objective lens 148A. In this manner, the subject can be illuminated uniformly with linearly polarized light beams when the emitters are disposed such that the center of gravity of a figure obtained by connecting a plurality of emitters that emit light beams polarized in the same direction coincides, for example, with the position of the objective lens in the imaging device. In addition, the subject can be illuminated uniformly with an unpolarized light beam when the centers of gravity of figures each obtained by connecting a plurality of emitters having a common polarization direction coincide with one another among the emitters that emit light beams having different polarization directions, which is thus more advantageous.

Operation of Image Forming Apparatus in First Mode

Hereinafter, an example of the operation of the image forming apparatus 100A will be described. In the following section, an object having a transparent or semi-transparent and smooth surface is illustrated as an example of the subject. Examples of such an object includes an eyeball of an organism (e.g., human or animal) and a transparent package for a tablet, and the subject is assumed to be a human eyeball herein.

First, a typical operation in the first mode will be described.

As described above, in the first mode, the illumination control circuit 162 (refer to FIG. 1) controls the illumination device 120A such that, of the plurality of light sources 124, the light sources 124 disposed behind the polarizers 126 of which the directions of the transmission axes coincide with one another are selectively turned on. Herein, the light sources 124 of the emitters 122a, the light sources 124 of the emitters 122b, and the light sources 124 of the emitters 122c are selectively and successively turned on. With such driving, the subject is irradiated successively with a first linearly polarized light beam having a polarization direction of 30°, a second linearly polarized light beam having a polarization direction of 90°, and a third linearly polarized light beam having a polarization direction of 150°.

Figure 3:
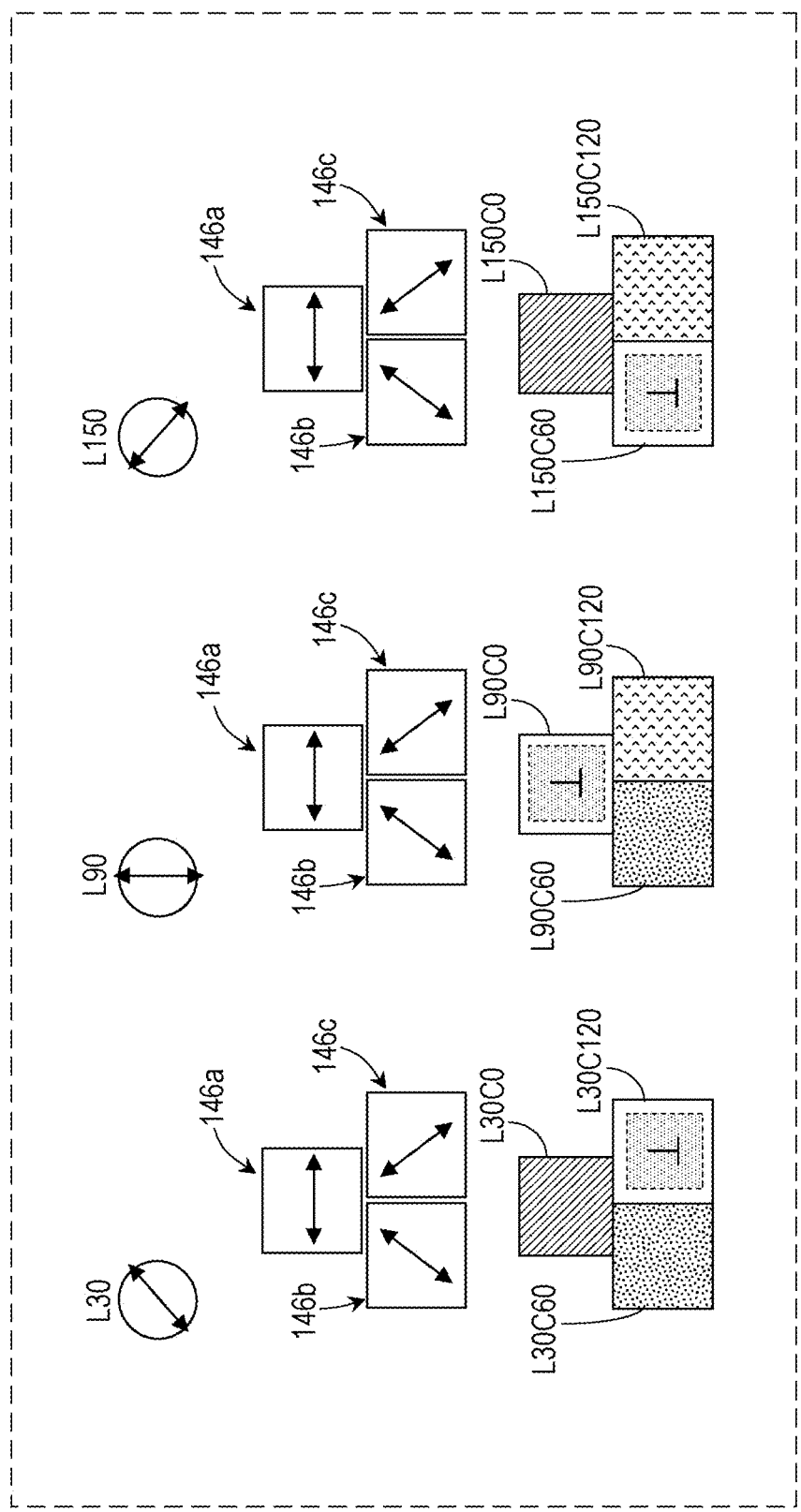
FIG. 3 is a schematic diagram for a describing a polarization image acquired by an imaging device in a first mode.

FIG. 3 is a schematic diagram for describing polarization images acquired by the imaging device 140A in the first mode. In FIG. 3, the correspondence between the polarization directions of light beams incident on the image sensors 142a, 142b, and 142c of the imaging device 140A and three polarization images acquired by the imaging device 140A when the subject is irradiated with the first linearly polarized light beam is schematically illustrated in the left side. Hereinafter, in the present specification and in the drawings, a linearly polarized light beam having a polarization direction of x degrees with which the subject is irradiated is denoted by Lx, and an image that is acquired when the subject is illuminated with an illumination light beam Lx and that is based on a light beam of which the vibration direction of the electric field vector is y degree is denoted by LxCy. For example, a polarization image that is acquired when the subject is illuminated with a linearly polarized light beam having a polarization direction of 30° and that is based on a light beam of which the polarization direction is 0° is expressed as L30C0.

When the light sources 124 of the emitters 122a are being selectively turned on, the subject (a human eyeball in this case) is irradiated with the first linearly polarized light beam having a polarization direction of 30°. A human eyeball has a cornea having a transparent and smooth surface, and the illumination light beam from the emitters 122a is reflected at and in the vicinity of the surface of the eyeball, resulting in little change in the polarization state. A returning light beam from the subject is split into three light beams by the beam splitter 144A, and the image sensor 142a, the image sensor 142b, and the image sensor 142c receive the light beams that have passed through the analyzers 146a, 146b, and 146c, respectively. For example, a light beam polarized in the direction of 0° is incident on the image sensor 142a.

As illustrated schematically in the left side of FIG. 3, when the subject is irradiated with an illumination light beam L30 having a polarization direction of 30°, the imaging device 140A captures polarization images L30C0, L30C60, and L30C120 with the image sensor 142a, the image sensor 142b, and the image sensor 142c, respectively. Among these polarization images, the polarization image L30C120 is a crossed-Nicols image in which the polarization direction of a light beam with which the subject is irradiated and the polarization direction of a light beam incident on the image sensor are orthogonal to each other.

Next, the illumination control circuit 162 selectively turns on the light sources 124 of the emitters 122b. In FIG. 3, a group of three polarization images acquired by the imaging device 140A in this case is schematically illustrated in the middle. When the light sources 124 of the emitters 122b are being selectively turned on, the subject is irradiated with the second linearly polarized light beam having a polarization direction of 90°. In this case, the imaging device 140A captures polarization images L90C0, L90C60, and L90C120. Among these polarization images, the polarization image L90C0 is a crossed-Nicols image.

Furthermore, the illumination control circuit 162 selectively turns on the light sources 124 of the emitters 122c. As schematically illustrated in the right side of FIG. 3, when the light sources 124 of the emitters 122c are being selectively turned on, the subject is irradiated with the third linearly polarized light beam having a polarization direction of 150°. In this case, the imaging device 140A captures polarization images L150C0, L150C60, and L150C120. Among these polarization images, the polarization image L150C60 is a crossed-Nicols image. As can be seen from FIG. 3, the polarization images L30C0, L90C0, and L150C0 are all images formed by signals of light beams incident on the first region Ra of the imaging device 140A, and the polarization images L30C60, L90C60, and L150C60 are all images formed by signals of light beams incident on the second region Rb of the imaging device 140A. The polarization images L30C120, L90C120, and L150C120 are all images formed by signals of light beams incident on the third region Rc of the imaging device 140A.

The image forming circuit 164 (refer to FIG. 1) generates an image of the subject on the basis of the total of nine polarization images acquired with the polarization state of the illumination light beam being varied. Hereinafter, an example of the processing of the image forming circuit 164 will be described.

Figure 4:
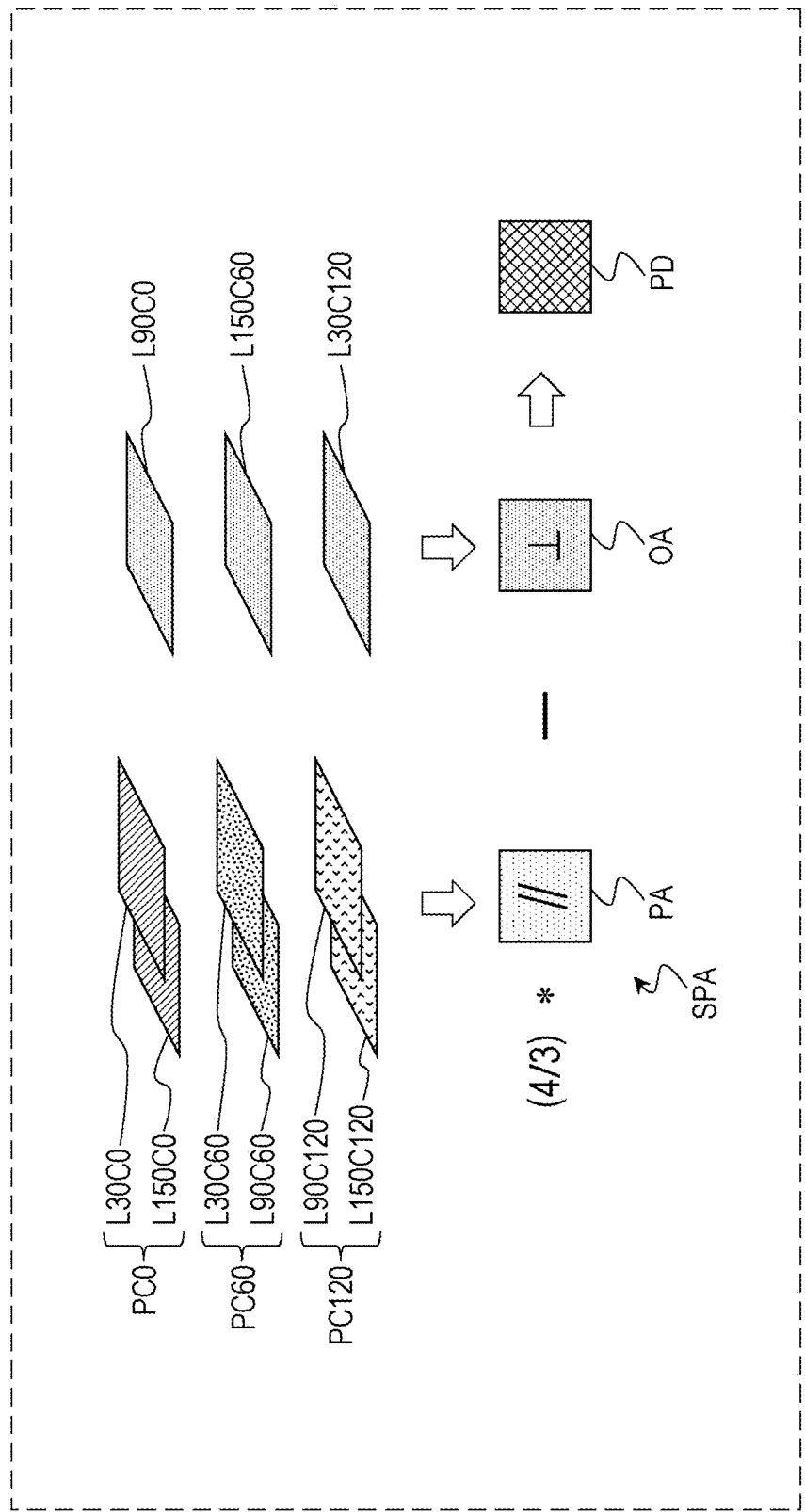
FIG. 4 is a schematic diagram illustrating an overview of typical processing of an image forming circuit.

FIG. 4 illustrates an outline of typical processing of the image forming circuit 164. In the example described herein, broadly speaking, the image forming circuit 164 generates, as an image of the subject, data of a polarization subtraction image resulting from subtraction processing of an averaged parallel-Nicols image and an averaged crossed-Nicols image. As described in Kanamori, image data in which a contrast associated with fine concavities and convexities in the surface of a subject is enhanced can be obtained by acquiring a parallel-Nicols image and a crossed-Nicols image of the subject and by obtaining the difference between these images. Useful information pertaining to a flaw, a foreign object, and the like on the subject can be obtained on the basis of the difference between a parallel-Nicols image and a crossed-Nicols image.

In the techniques described in Kanamori and in Japanese Unexamined Patent Application Publication No. 2015-164518, a parallel-Nicols image and a crossed-Nicols image are acquired under each of an illumination light beam having a polarization direction of 0° and an illumination light beam having a polarization direction of 90°. Furthermore, the parallel-Nicols images and the crossed-Nicols images acquired under the illumination light beams having different polarization directions are each averaged, and the difference between the averaged images is obtained. This processing can be expressed as (L0C0+L90C90)/2−(L0C90+L90C0)/2 with the use of the expressions of the polarization images in the present specification. One of the reasons why such processing is employed is as follows. When a different set of an image sensor and an analyzer is used to acquire parallel-Nicols images and crossed-Nicols image, for example, and when these images are simply subjected to the subtraction processing, relatively large noise may be produced in the result of the subtraction processing resulting from the difference in the characteristics of the imaging optical systems used to acquire the images.

As described with reference to FIG. 3, each of a set of three polarization images obtained under the irradiation of the first linearly polarized light beam, a set of three polarization images obtained under the irradiation of the second linearly polarized light beam, and a set of three polarization images obtained under the irradiation of the third linearly polarized light beam includes one crossed-Nicols image without fail. Therefore, as schematically illustrated in FIG. 4, an averaged crossed-Nicols image OA is formed by averaging the crossed-Nicols images L30C120, L90C0, and L150C60 obtained under the irradiation of the respective linearly polarized light beams. Herein, the term "to average" means to calculate an arithmetic mean of pixel values of corresponding pixels among a plurality of images. Therefore, the averaged crossed-Nicols image OA can be expressed as (L30C120+L90C0+L150C60)/3.

Figure 5:
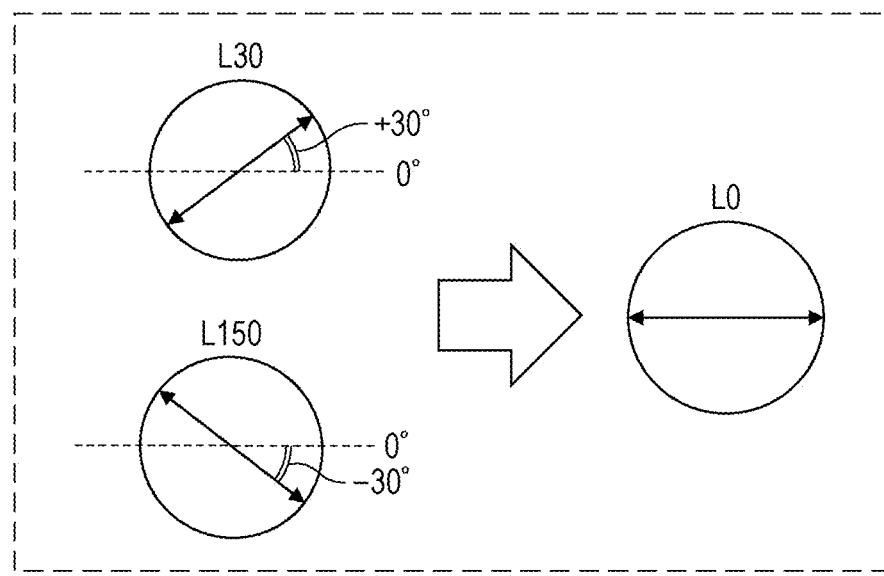
FIG. 5 is an illustration for describing an effect obtained by combining polarization images.

Meanwhile, the total of nine polarization images obtained with the polarization direction being varied do not include a parallel-Nicols image. Therefore, three sets of two polarization images are selected from the six polarization images other than the crossed-Nicols images, and three pseudo-parallel-Nicols images are formed. For example, when the polarization images L30C0 and L150C0 are considered, the polarization directions of the linearly polarized light beams with which the subject is irradiated when these polarization images are acquired are at the angles inclined by ±30° with respect to 0°, or the direction of the transmission axis of the analyzer 146a, as schematically illustrated in FIG. 5. Therefore, an image PC0 (refer to FIG. 4) obtained by averaging the polarization images L30C0 and L150C0 can be regarded as an image that simulatively expresses a parallel-Nicols image to be obtained when the subject is irradiated with a linearly polarized light beam having a polarization direction of 0°. In a similar manner, an image PC60 (refer to FIG. 4) obtained by averaging the polarization images L30C60 and L90C60 can be said to simulatively express a parallel-Nicols image to be obtained under the irradiation of a linearly polarized light beam having a polarization direction of 60°, and an image PC120 (refer to FIG. 4) obtained by averaging the polarization images L90C120 and L150C120 can be said to simulatively express a parallel-Nicols image to be obtained under the irradiation of a linearly polarized light beam having a polarization direction of 120°.

Averaging the image PC0, the image PC60, and the image PC120 can be said to provide a result similar to the result obtained by averaging the parallel-Nicols images obtained under the linearly polarized light beams having respective polarization directions of 0°, 60°, and 120°. However, when the image PC0 is considered, for example, in the polarization images L30C0 and L150C0, the polarization directions of the linearly polarized light beams with which the subject is irradiated are inclined by 30° in the positive or negative direction with respect to the direction of the transmission axis of the analyzer 146a, and thus the intensity of the light beam incident on the image sensor 142a is $\cos^2 30°$ times the intensity obtained when the polarization directions of the linearly polarized light beams coincide with the direction of the transmission axis of the analyzer 146a. In consideration of this point, as schematically illustrated in FIG. 4, the image forming circuit 164 forms an image PA obtained by averaging the six polarization images other than the crossed-Nicols images and forms an averaged pseudo-parallel-Nicols image SPA by multiplying the image PA by the correction coefficient) $(1/\cos^2 30°)=(4/3)$. With the use of the LxCy representation system, the averaged pseudo-parallel-Nicols image SPA can be expressed as $(\frac{2}{3})*(L30C0+L150C0+L30C60+L90C60+L90C120+L150C120)/3$. In the above, "*" means multiplication.

Furthermore, the image forming circuit 164 forms, as an image of the subject, an image PD obtained by subjecting the averaged pseudo-parallel-Nicols image SPA and the averaged crossed-Nicols image OA to the subtraction processing. The image PD can be expressed as in the following expression (1).

$$\left(\frac{2}{3}\right)\frac{\left(\begin{array}{c}L30C0+L150C0+L30C60+\\L90C60+L90C120+L150C120\end{array}\right)}{3} - \qquad (1)$$
$$\frac{(L90C0+L150C60+L30C120)}{3}$$

The following expression (2) can be obtained by transforming the expression (1).

$$\left(\frac{1}{3}\right)\left[\left\{\left(\frac{4}{3}\right)\frac{(L30C0+L150C0)}{2}-L90C0\right\}+\qquad(2)$$
$$\left\{\left(\frac{4}{3}\right)\frac{(L30C60+L90C60)}{2}-L150C60\right\}+$$
$$\left\{\left(\frac{4}{3}\right)\frac{(L90C129+L150C120)}{2}-L30C120\right\}\right]$$

In the expression (2), for example, the first term within the square brackets corresponds to the difference between the parallel-Nicols image and the crossed-Nicols image that are based on the light beams that have passed through the analyzer of which the direction of the transmission axis is 0°. As can be seen from the expression (2), the image PD obtained in the end expresses a result that is substantially equivalent to the result obtained by averaging the difference between the parallel-Nicols image and the crossed-Nicols image that are based on the light beams that have passed through the analyzer of which the direction of the transmission axis is 0°, the difference between the parallel-Nicols image and the crossed-Nicols image that are based on the light beams that have passed through the analyzer of which the direction of the transmission axis is 60°, and the difference between the parallel-Nicols image and the crossed-Nicols image that are based on the light beams that have passed through the analyzer of which the direction of the transmission axis is 120°. In other words, the image PD provides a result similar to the result obtained by acquiring a parallel-Nicols image and a crossed-Nicols image by each of a set of the analyzer 146a and the image sensor 142a, a set of the analyzer 146b and the image sensor 142b, and a set of the analyzer 146c and the image sensor 142c, by obtaining the difference between the parallel-Nicols image and the crossed-Nicols image in each of the sets, and by averaging the three differences.

According to the above-described processing of obtaining the image PD on the basis of the difference between the averaged pseudo-parallel-Nicols image SPA and the averaged crossed-Nicols image OA, an influence of the difference in the optical path in the beam splitter 144A, an influence of the difference in the characteristics among the image sensors 142a to 142c, and so on are averaged in the course of the processing. Therefore, a deterioration in the image quality resulting from these differences can be suppressed. In addition, the expression (2) is also symmetric with respect to the polarization directions of the linearly polarized light beams with which the subject is irradiated. Thus, according to the processing described above, the characteristics of the light sources 124 in the emitters 122a to 122c are also averaged, and it can be seen that a high-quality image of the subject can be obtained.

Figure 6:
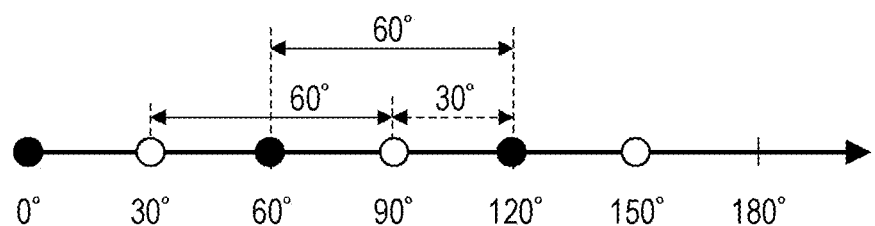
FIG. 6 illustrates a relationship between the direction of a transmission axis of a polarizer in an illumination device and the directions of transmission axes of analyzers.

FIG. 6 illustrates a relationship between the directions of the transmission axes of the polarizers 126 in the illumination device 120A and the directions of the transmission axes of the analyzers 146a to 146c. In FIG. 6, the open circles (○) indicate the directions of the transmission axes of the polarizers 126, and the solid circles (●) indicate the directions of the transmission axes of the analyzers 146a to 146c. As illustrated in FIG. 6, the directions of the transmission axes of the polarizers 126 included in the illumination device 120A are at an interval of 60°, that is, at 30°, 90°, and 150° and are distributed evenly within the range of from 0° to 180°. The direction of the transmission axis of the analyzer 146a, the direction of the transmission axis of the analyzer 146b, and the direction of the transmission axis of the analyzer 146c are at an interval of 60°, that is, at 0°, 60°, and 120°, respectively and are also distributed evenly within the range of from 0° to 180°. In addition, the interval between a pair of an open circle and a solid circle that are adjacent to each other is 30° for all the pairs.

The relationship between the polarization directions of the light beam incident on the first region Ra, the light beam incident on the second region Rb, and the beam light incident on the third region Rc and the polarization directions of the linearly polarized light beams that illuminate the subject in the first mode is also similar to the relationship between the three open circles and the three solid circles in the graph illustrated in FIG. 6. As illustrated in FIG. 6, in a typical embodiment of the present disclosure, the directions of the transmission axes of the polarizers and of the analyzers are selected, for example, such that the three open circles and the three solid circles are evenly distributed. When the three open circles and the three solid circles are evenly distributed within the range of 180° as in the example illustrated in FIG. 6, the three polarization directions of the illumination light beams and the three polarization directions of the light beams incident on the imaging surface can be used in a well-balanced manner among the nine polarization images, which is thus advantageous. As a result, an effect of the evenness of the polarization directions of the illumination light beams and of the light beams incident on the imaging surface can be obtained in the formation of the averaged pseudo-parallel-Nicols image SPA and the averaged crossed-Nicols image OA.

Figure 7:
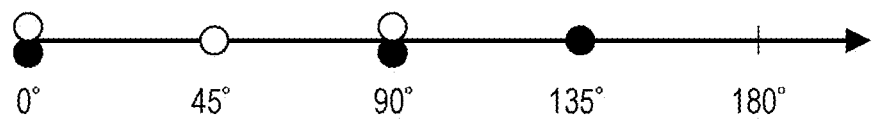
FIG. 7 illustrates, as a comparative example, a relationship between the direction of a transmission axis of a polarizer on the illumination side and the direction of a transmission axis of an analyzer on the imaging side in the endoscopic apparatus described in Ji Qi, et. al.

FIG. 7 illustrates, as a comparative example, a relationship between the directions of the transmission axes of the polarizers on the illumination side and the directions of the transmission axes of the analyzers on the imaging side in the endoscopic apparatus described in Ji Qi, et. al. described above. In FIG. 7, the open circles (○) indicate the directions of the transmission axes of the polarizers on the illumination side and the solid circles (●) indicate the directions of the transmission axes of the analyzers on the imaging side.

In this example, for each of the three open circles, a corresponding solid circle is present at a position spaced apart by 90°. In other words, selecting the directions of the transmission axes in this manner makes it possible to obtain three crossed-Nicols images. In addition, since a pair of an open circle and a solid circle is present at each of the positions of 0° and 90°, parallel-Nicols images of which the polarization directions of the illumination light beams are 0° and 90° can be obtained. However, a parallel-Nicols image of which the polarization direction of the illumination light beam is 135° cannot be obtained, and thus it is not possible to apply the difference between the averaged pseudo-parallel-Nicols image SPA and the averaged crossed-Nicols image OA as described above. In addition, in this example, although the interval between two adjacent open circles is 45°, an open circle is not present at the position of 135°, and the directions of the transmission axes of the polarizers are unevenly distributed within the range of 180°. With regard to the analyzers on the imaging side, the interval between two adjacent solid circles is 90° or 45°, and the solid circles are not at equal intervals. Therefore, even when an image corresponding to a parallel-Nicols image of which the polarization direction of the illumination light beam is 45° is generated separately and the subtraction processing of the averaged pseudo-parallel-Nicols image SPA and the averaged crossed-Nicols image OA is applied, an effect of averaging cannot be obtained at a sufficient level. When the directions of the transmission axes of the polarizers are selected in this manner, it is difficult to obtain an unpolarized light beam even if three types of polarized light beams having different polarization directions are mixed.

According to the processing of obtaining the difference between the averaged pseudo-parallel-Nicols image SPA and the averaged crossed-Nicols image OA described with reference to FIG. 4, the following additional advantages can be obtained.

Figure 8:
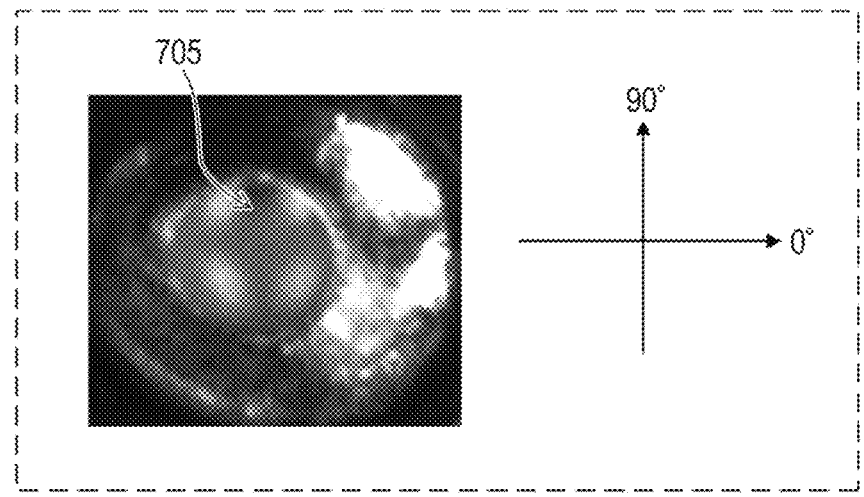
FIG. 8 illustrates an example of a crossed-Nicols image obtained when an image of an eyeball of an organism is captured under the illumination of a linearly polarized light beam having a polarization direction of 0°.
Figure 9:
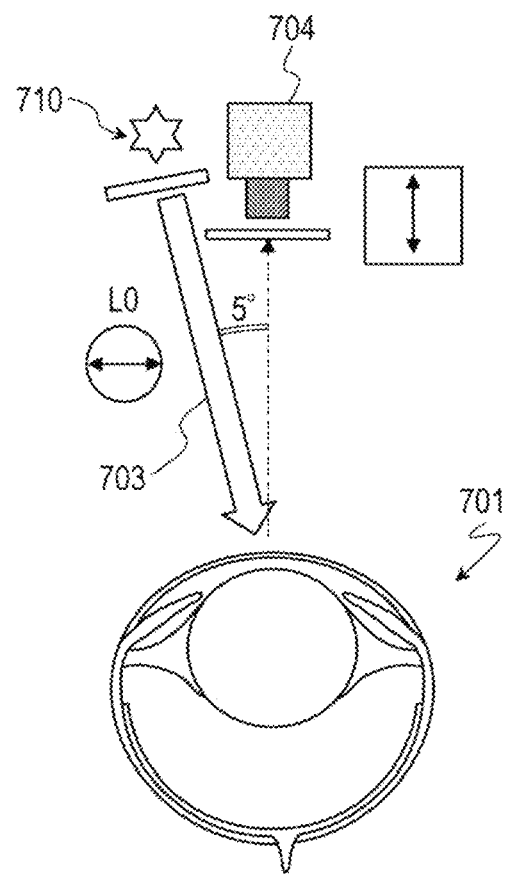
FIG. 9 is a schematic diagram illustrating the arrangement of a light source, a subject, and a camera when the crossed-Nicols image illustrated in FIG. 8 is acquired.

FIG. 8 illustrates an example of a crossed-Nicols image obtained when an image of an eyeball of an organism is captured under the irradiation of a linearly polarized light beam having a polarization direction of 0°. FIG. 9 illustrates the arrangement of the light source, the subject, and the camera when the crossed-Nicols image illustrated in FIG. 8 is acquired. Herein, a fish eyeball is selected as a subject 701, and an image is captured with a light source 710 disposed in the direction of 5°, which is close to be coaxial, with respect to the straight line connecting the subject 701 and a camera 704, as schematically illustrated in FIG. 9. A polarizer of which the direction of the transmission axis is 0° is disposed between the light source 710 and the subject 701. An analyzer of which the direction of the transmission axis is 90° is disposed between the subject 701 and the camera 704. In this example, the subject 701 is irradiated with a light beam having a polarization direction of 0°.

As illustrated in FIG. 8, when a crossed-Nicols image is acquired with an eyeball of an organism serving as a subject, a cross-shaped dark pattern 705 may appear in the image. As can be seen from FIG. 8, the dark pattern 705 appears at the position of the pupil. Such a dark pattern 705 is considered to appear due to the birefringence characteristics of the cornea and the crystalline lens of the eyeball. An appearance of such a dark pattern 705 can result in the deterioration of the image of the subject. In addition, in the example illustrated in FIG. 8, the dark pattern 705 includes a portion that extends in the direction of 0° and a portion that extends in the direction of 90°. In other words, it can be seen that a dark portion appears so as to extend in the polarization direction of the incident linearly polarized light beam and in the direction parallel to the direction orthogonal to the polarization direction. Therefore, it is speculated that the anisotropy of the vibration direction of the electric field vector in the illumination light beam affects the occurrence of the dark pattern 705.

In this manner, in a simply acquired crossed-Nicols image when an eyeball of an organism serves as a subject, a dark pattern 705 is mixed into the image, and thus accurate information on the subject may not be obtained. As will be described hereinafter, an influence of such a dark pattern can be removed through the processing of forming an image PD as the image of the subject.

Figure 10:
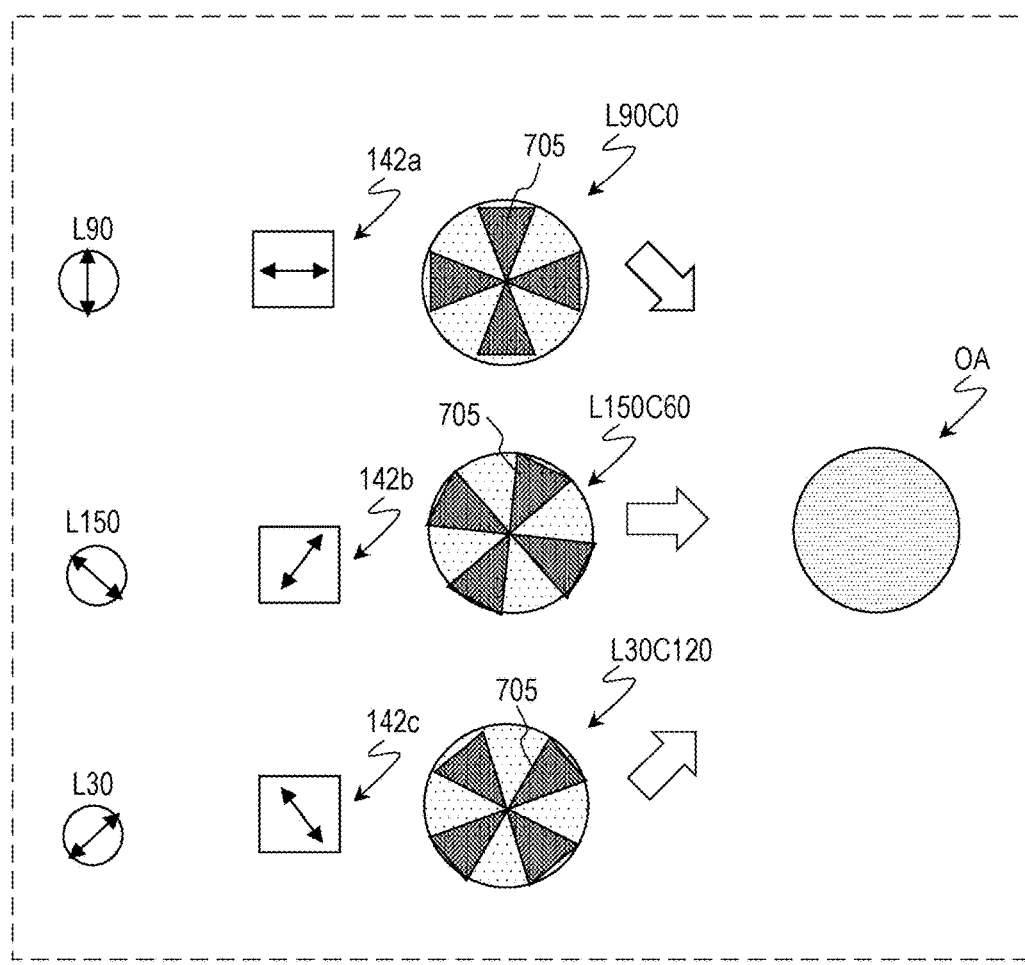
FIG. 10 is a schematic diagram for describing the principle of removing an influence of a cross-shaped dark pattern by forming an averaged crossed-Nicols image.

FIG. 10 schematically illustrates the principle of removing an influence of a cross-shaped dark pattern by forming an averaged crossed-Nicols image OA. As described with reference to FIG. 3, in a typical embodiment of the present disclosure, one crossed-Nicols image is acquired for each of the polarization directions of the illumination light beams. As schematically illustrated in FIG. 10, these crossed-Nicols images (the polarization images L90C0, L150C60, and L30C120 in this case) may each include a cross-shaped dark pattern 705. However, the directions in which the dark portions of the cross-shaped dark patterns 705 extend differ among these images. For example, the dark portions appearing in the polarization image L90C0 extend in the directions of 0° and 90°, and the dark portions appearing in the polarization image L150C60 extend in the directions of 60° and 150°. In other words, as the polarization directions of the illumination light beams differ by 60°, the directions in which the dark portions extend also differ by 60° between the polarization images L90C0 and L150C60.

As schematically illustrated in FIG. 10, the averaged crossed-Nicols image OA can be formed by combining the polarization images L90C0, L150C60, and L30C120. Since the directions in which the dark portions extend differ by 60° among the different polarization images, the dark patterns 705 in the polarization images are spatially averaged. Herein, the polarization directions of the illumination light beams differ by 60° among the three polarization images, and thus the dark patterns 705 in the polarization images are evenly averaged, and an averaged crossed-Nicols image OA in which the an influence of the dark patterns 705 is removed is formed as a result. In other words, the image PD serving as an image of the subject results in an image in which an influence of the dark patterns 705 is removed.

A reference plane, a second plane obtained by rotating a reference line included in the reference plane by 30 degrees in a first direction, a fourth plane obtained by rotating the reference line by 90 degrees in the first direction, and a sixth plane obtained by rotating the reference line by 150 degrees in the first direction may be assumed.

Each of the plurality of emitters 122a may include a first polarizer that transmits a light beam vibrating in a first plane parallel to the second plane and that does not transmit a light beam vibrating in a plane that is not parallel to the second plane. The plurality of emitters 122a may illuminate the subject with first light beams that vibrate in a plurality of first planes in a first period. Each of the plurality of emitters 122b may include a second polarizer that transmits a light beam vibrating in a third plane parallel to the fourth plane and that does not transmit a light beam vibrating in a plane that is not parallel to the third plane. The plurality of emitters 122b may illuminate the subject with second light beams that vibrate in a plurality of third planes in a second period. Each of the plurality of emitters 122c may include a third polarizer that transmits a light beam vibrating in a fifth plane parallel to the sixth plane and that does not transmit a light beam vibrating in a plane that is not parallel to the fifth plane. The plurality of emitters 122c may illuminate the subject with third light beams that vibrate in a plurality of fifth planes in a third period. The first period need not overlap the second period, the first period need not overlap the third period, and the second period need not overlap the third period.

A beam splitter may receive a first reflection light beam resulting as the first light beam is reflected at the subject and output a first deflection light beam, a second deflection light beam, and a third deflection light beam, may receive a second reflection light beam resulting as the second light beam is reflected at the subject and output a fourth deflection light beam, a fifth deflection light beam, and a sixth deflection light beam, and may receive a third reflection light beam resulting as the third light beam is reflected at the subject and output a seventh deflection light beam, an eighth deflection light beam, and a ninth deflection light beam. The beam splitter constituted by the beam splitter 144A may include a first analyzer constituted by the analyzer 146a, a second analyzer constituted by the analyzer 146b, and a third analyzer constituted by the analyzer 146c. The beam splitter may split the received first reflection light beam to generate a first split light beam, a second split light beam, and a third split light beam. The first analyzer may receive the first split light beam and output the first deflection light beam. The second analyzer may receive the second split light beam and output the second deflection light beam. The third analyzer may receive the third split light beam and output the third deflection light beam. The beam splitter may split the received second reflection light beam to generate a fourth split light beam, a fifth split light beam, and a sixth split light beam. The first analyzer may receive the fourth split light beam and output the fourth deflection light beam. The second analyzer may receive the fifth split light beam and output the fifth deflection light beam. The third analyzer may receive the sixth split light beam and output the sixth deflection light beam. The beam splitter may split the received third reflection light beam to generate a seventh split light beam, an eighth split light beam, and a ninth split light beam. The first analyzer may receive the seventh split light beam and output the seventh deflection light beam. The second analyzer may receive the eighth split light beam and output the eighth deflection light beam. The third analyzer may receive the ninth split light beam and output the ninth deflection light beam.

Each of the first deflection light beam, the fourth deflection light beam, and the seventh deflection light beam may vibrate in a seventh plane parallel to the reference plane, each of the second deflection light beam, the fifth deflection light beam, and the eighth deflection light beam may vibrate in an eighth plane parallel to a ninth plane obtained by rotating the reference line included in the reference plane by 60 degrees in the first direction, and each of the third deflection light beam, the sixth deflection light beam, and the ninth deflection light beam may vibrate in a tenth plane parallel to an eleventh plane obtained by rotating the reference line in the reference plane by 120 degrees in the first direction.

The image sensor 142a may include a plurality of first pixels, the image sensor 142b may include a plurality of second pixels, and the image sensor 142c may include a plurality of third pixels. The plurality of first pixels may correspond one-to-one to the plurality of second pixels, and the plurality of first pixels may correspond one-to-one to the plurality of third pixels.

The plurality of first pixels may receive the first deflection light beam and output a polarization image L30C0 that includes a plurality of first pixel values corresponding to the respective first pixels. The plurality of second pixels may receive the second deflection light beam and output a polarization image L30C60 that includes a plurality of second pixel values corresponding to the respective second pixels. The plurality of third pixels may receive the third deflection light beam and output a polarization image L30C120 that includes a plurality of third pixel values corresponding to the respective third pixels. The plurality of first pixels may receive the fourth deflection light beam and output a polarization image L90C0 that includes a plurality of fourth pixel values corresponding to the respective first pixels. The plurality of second pixels may receive the fifth deflection light beam and output a polarization image L90C60 that includes a plurality of fifth pixel values corresponding to the respective second pixels. The plurality of third pixels may receive the sixth deflection light beam and output a polarization image L90C120 that includes a plurality of sixth pixel values corresponding to the respective third pixels. The plurality of first pixels may receive the seventh deflection light beam and output a polarization image L150C0 that includes a plurality of seventh pixel values corresponding to the respective first pixels. The plurality of second pixels may receive the eighth deflection light beam and output a polarization image L150C60 that includes a plurality of eighth pixel values corresponding to the respective second pixels. The plurality of third pixels may receive the ninth deflection light beam and output a polarization image L150C120 that includes a plurality of ninth pixel values corresponding to the respective third pixels.

The image forming circuit may calculate a pixel value $p(i)=(p1(i)+p2(i)+p5(i)+p6(i)+p7(i)+p9(i))\times(2/3)-(p3(i)+p4(i)+p8(i))/3$ and generate an image of the subject on the basis of the calculated pixel value. The pixel value $p1(i)$ may be included in the plurality of first pixel values, the pixel value $p2(i)$ may be included in the plurality of second pixel values, the pixel value $p3(i)$ may be included in the plurality of third pixel values, the pixel value $p4(i)$ may be included in the plurality of fourth pixel values, the pixel value $p5(i)$ may be included in the plurality of fifth pixel values, the pixel value $p6(i)$ may be included in the plurality of sixth pixel values, the pixel value $p7(i)$ may be included in the plurality of seventh pixel values, the pixel value $p8(i)$ may be included in the plurality of eighth pixel values, and the pixel value $p9(i)$ may be included in the plurality of ninth pixel values. The pixel value $p1(i)$ may correspond to $p2(i)$, $p3(i)$, $p4(i)$, $p5(i)$, $p6(i)$, $p7(i)$, $p8(i)$, and $p9(i)$, and the i may be a natural number.

The position of the pixel corresponding to the pixel value $p(i)$ in the image of the subject may be the position of the pixel corresponding to $p1(i)$ among the positions of the pixels included in the polarization image L30C0, the position of the pixel corresponding to p2(i) among the positions of the pixels included in the polarization image L30C60, the position of the pixel corresponding to p3(i) among the positions of the pixels included in the polarization image L30C120, the position of the pixel corresponding to p4(i) among the positions of the pixels included in the polarization image L90C0, the position of the pixel corresponding to p5(i) among the positions of the pixels included in the polarization image L90C60, the position of the pixel corresponding to p6(i) among the positions of the pixels included in the polarization image L90C120, the position of the pixel corresponding to p7(i) among the positions of the pixels included in the polarization image L150C0, the position of the pixel corresponding to p8(i) among the positions of the pixels included in the polarization image L150C60, or the position of the pixel corresponding to p9(i) among the positions of the pixels included in the polarization image L150C120.

Operation of Image Forming Apparatus in Second Mode

Next, a typical operation in the second mode will be described.

The second mode is useful for estimating the shape of an object having a transparent or semi-transparent and smooth surface. In the second mode, the subject is irradiated with an unpolarized light beam, and image data that is based on a returning light beam from the subject is acquired. The technique in which a subject is irradiated with an unpolarized light beam and the shape of the subject is estimated on the basis of the polarization state of a returning light beam from the subject is referred to as Shape from Polarization. As described in Gary A. Atkinson et. al., in Shape from Polarization, an analyzer on the camera side is rotated in a state in which a subject is globally irradiated with an unpolarized light beam, and at least three images of which the directions of the transmission axis of the analyzer differ from one another are acquired. As will be described hereinafter, according to an embodiment of the present disclosure, an image forming apparatus that can acquire image data necessary for Shape from Polarization without an illumination optical system and an imaging optical system being separately provided can be provided.

Figure 11:
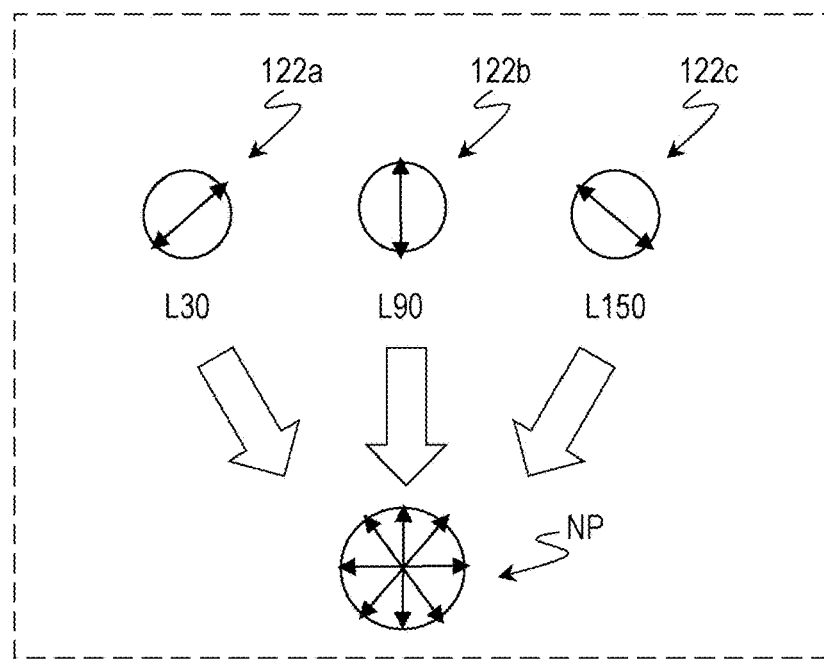
FIG. 11 is a schematic diagram for describing an operation of an illumination device in a second mode.

FIG. 11 is a schematic diagram for describing an operation of the illumination device 120A in the second mode. In the second mode, the illumination control circuit 162 (refer to FIG. 1) turns on the light sources 124 of the emitters 122a, the emitters 122b, and the emitters 122c simultaneously. In other words, the illumination device 120A irradiates the subject simultaneously with a light beam having a polarization direction of 30°, a light beam having a polarization direction of 90°, and a light beam having a polarization direction of 150°. As this point, as schematically illustrated in FIG. 11, the linearly polarized light beams from the emitters 122a, 122b, and 122c are mixed, and the subject is irradiated with an illumination light beam NP that is substantially unpolarized.

Figure 12:
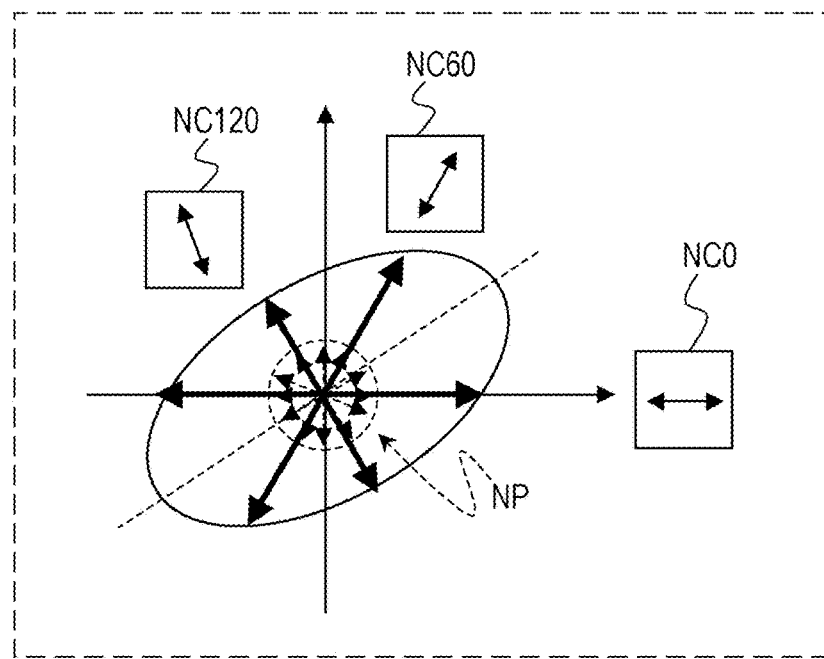
FIG. 12 schematically illustrates a relationship between the polarization state of a returning light beam from a subject and three polarization images acquired by an imaging device.

FIG. 12 schematically illustrates a relationship between the polarization state of a returning light beam from the subject and three polarization images acquired by the imaging device 140A. As schematically illustrated in FIG. 12, the returning light beam from the subject is partially polarized. When the subject is irradiated with the illumination light beam NP from the illumination device 120A, the image sensor 142a of the imaging device 140A acquires a polarization image NC0 that is based on, of the returning light beam from the subject, a light beam having a polarization direction of 0°. The image sensors 142b and 142c acquire a polarization image NC60 that is based on, of the returning light beam from the subject, a light beam having a polarization direction of 60° and a polarization image NC120 that is based on a light beam having a polarization direction of 120°, respectively.

In this manner, with the image forming apparatus 100A, data of the three polarization images NC0, NC60, and NC120 that can be used for Shape from Polarization can be acquired by switching the light sources to be turned on in accordance with the selected mode without adding any modification to the configuration of the illumination optical system and the imaging optical system. In addition, these three polarization images can be acquired in a single instance of imaging, and the time it takes for imaging can be reduced as compared to the existing technique in which imaging is carried out at least three times with the angle of the analyzer being varied.

When the polarization images NC0, NC60, and NC120 can be acquired, the shape of the subject can be estimated on the basis of the polarization images NC0, NC60, and NC120 by applying the technique such as the one described in Daisuke Miyazaki, et. al. or in Gary A. Atkinson et. al. For example, when imaging is carried out with the analyzer being rotated as described in Gary A. Atkinson et. al., the intensity of the light beam transmitted through the analyzer (may also be said to be a luminance value of a pixel in the obtained image) may show a change of a sinusoidal function with a cycle of 180°. As at least three images of the subject are obtained with the angle of the analyzer being varied, the sine curve that represents the intensity of the light beam transmitted through the analyzer can be determined. This sine curve is a function of the phase angle $\phi$ and the rotation angle $\theta_p$ of the analyzer, and the azimuth of the vector normal to the surface of the subject can be determined from the phase angle $\phi$ when the stated sine curve can be determined. In addition, the degree $\rho$ of polarization can be determined on the basis of the stated sine curve, and the zenith angle of the normal vector can be determined from the degree $\rho$ of polarization. The phase angle $\phi$ is an angle formed by the reference direction and the vibration direction of the electric field vector of a polarization component of the returning light beam of which the amplitude of the electric field vector is largest, and the function that expresses the sine curve takes a maximum value when $\phi=\theta_p$ holds. For reference, the entire content disclosed in each of Daisuke Miyazaki, et. al. and Gary A. Atkinson et. al. is incorporated herein.

Figure 13:
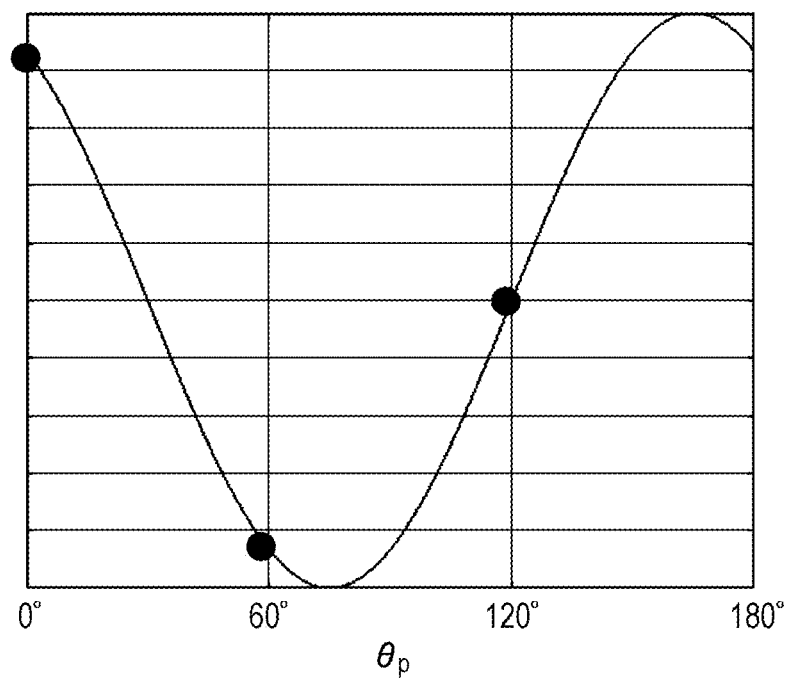
FIG. 13 illustrates a relationship between the directions of the transmission axes of analyzers in an image forming apparatus and a sine curve determined on the basis of a polarization image acquired when the directions of the stated transmission axes are set as shown.

FIG. 13 illustrates a relationship between the directions of the transmission axes of the analyzers 146a, 146b, and 146c in the image forming apparatus 100A and a sine curve determined on the basis of the polarization images acquired when the directions of the stated transmission axes are set as shown. The solid circles (●) illustrated in FIG. 13 indicate the directions of the transmission axes of the analyzers 146a to 146c. The graph illustrated in FIG. 13 is a sine curve determined on the basis of the polarization images NC0, NC60, and NC120 and represents a change in the luminance value of a pixel in an image obtained when imaging is to be carried out with the angle of the analyzer being varied.

In a typical embodiment of the present disclosure, polarization images of the light beams of which the polarization directions differ from one another by 60° can be acquired in a single instance of imaging. As described with reference to FIG. 6, the solid circles indicating the directions of the transmission axes of the analyzers 146a to 146c are evenly distributed at an interval of 60° in the range of 180°. Therefore, it can be expected that, when the three polarization images acquired in the second mode are used, a sine curve can be determined with high accuracy as compared to a case in which imaging is carried out with the analyzer being rotated at an interval of 45°, that is, at 0°, 45°, and 90° as in Gary A. Atkinson et. al., for example. For a similar reason, a typical embodiment of the present disclosure has an advantage over the configuration described in Ji Qi et. al. (refer to FIG. 7) in which imaging is carried out with the directions of the transmission axis of the analyzer on the imaging side being set at 0°, 90°, and 135° (−45°). In addition, as can be seen from FIG. 6, in a typical embodiment of the present disclosure, the directions of the transmission axes of the polarizers 126 are selected so as to be evenly distributed within the range of 180°, and thus the three parameters including the amplitude, the mean, and the phase of the sine curve can be determined with high accuracy.

Figure 14:
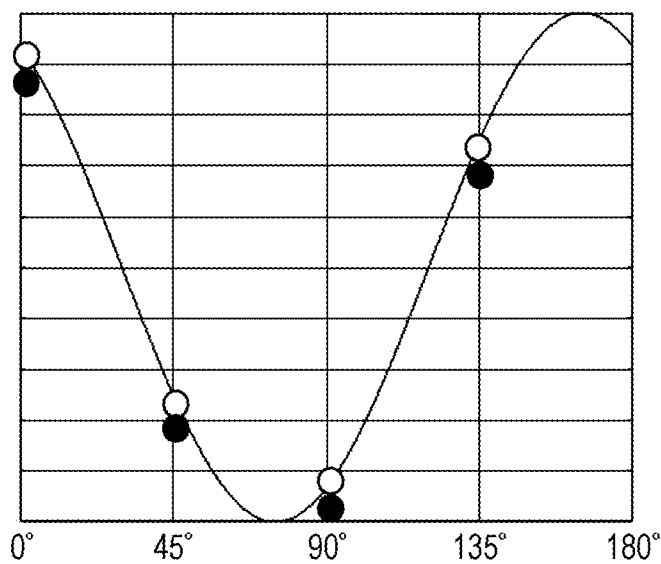
FIG. 14 illustrates, as a comparative example, a relationship between the polarization direction of a light beam emitted from a polarization irradiator toward a subject and the polarization direction of a light beam incident on a CCD camera in the endoscopic apparatus described in Japanese Unexamined Patent Application Publication No. 2012-045029.

FIG. 14 illustrates, as a comparative example, a relationship between the polarization directions of the light beams with which a subject is irradiated by the polarization irradiator and the polarization directions of the light beams incident on the CCD camera in the endoscopic apparatus described in Japanese Unexamined Patent Application Publication No. 2012-045029 described above. The open circles (○) and the solid circles (●) illustrated in FIG. 14 indicate the polarization directions of the light beams emitted from the polarization irradiator and the polarization directions of the light beams incident on the CCD camera. In this example, four open circles and four solid circles are located at 0°, 45°, 90°, and 135° (−45°).

In the comparative example illustrated in FIG. 14, the four open circles and the four solid circles are arranged at an interval of 45°. The selection of the polarization directions illustrated in FIG. 14 is effective in terms of evenly distributing the polarization directions within the range of 180°. However, when four polarization images of light beams of which the polarization directions differ from one another by 45° are to be acquired at once for applying Shape from Polarization, a polarization mosaic filter, for example, is necessary, which renders it necessary to employ a complex optical system.

According to a typical embodiment of the present disclosure, three polarization images can be obtained in a single instance of imaging, and thus the time it takes to capture images necessary for estimating the shape of the subject can be reduced. In addition, since the three polarization directions of the light beams incident on the imaging surface are set evenly within the range of 180°, the calculation necessary for estimating the shape of the subject can be executed efficiently. The functions of the illumination control circuit 162 and the image forming circuit 164 described above may be implemented through a combination of a general purpose processing circuit and software or may be implemented by hardware dedicated to such processing. The first mode and the second mode described above may be executed successively and continually, or the imaging of a subject in the second mode may be executed with an interval after the imaging of the same subject in the first mode is executed. Which mode is to be executed first may be determined as desired. In one or both of the first mode and the second mode, imaging may be repeated with the polarization plane of the illumination light beam being varied.

Second Embodiment

Figure 15:
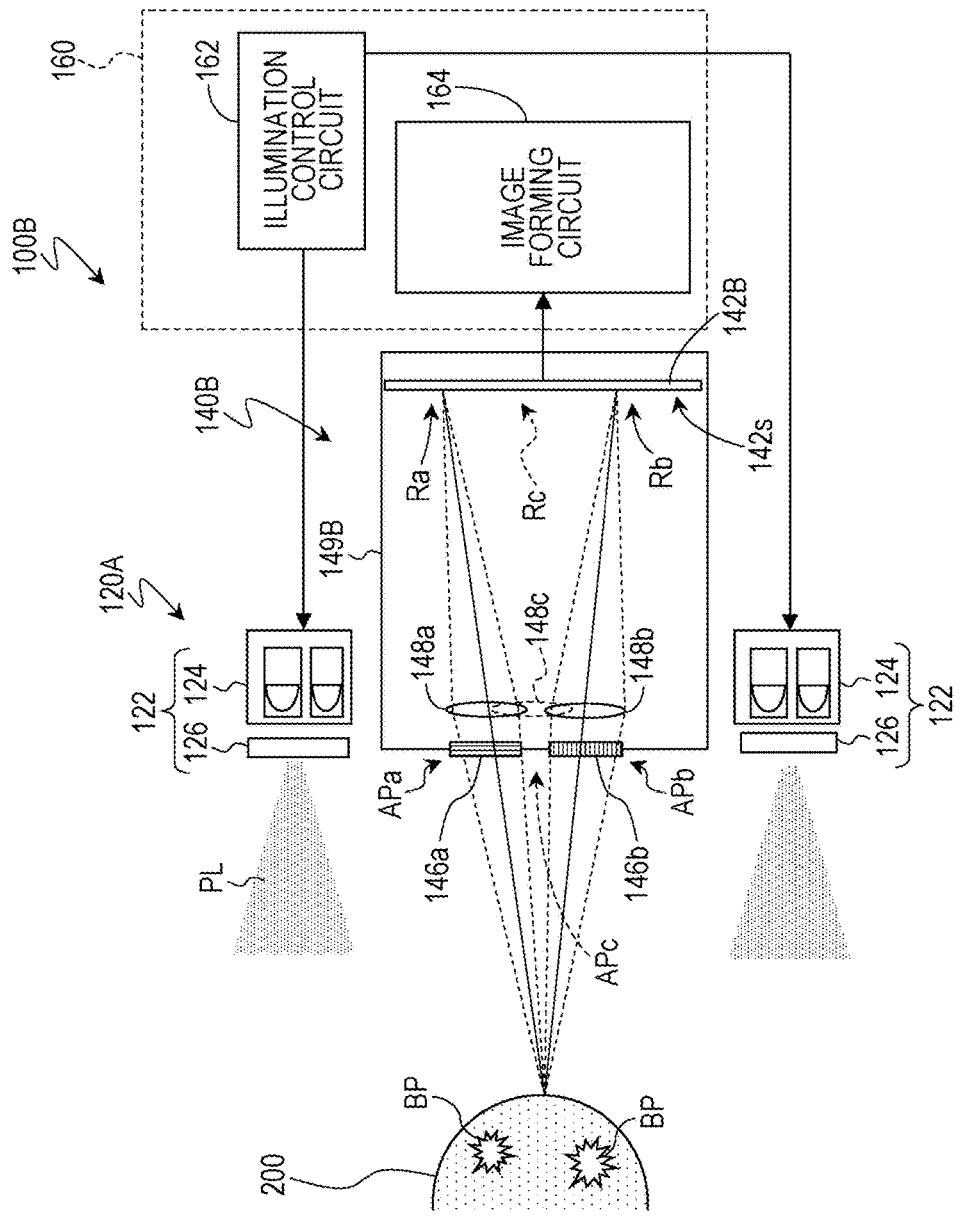
FIG. 15 illustrates an exemplary configuration of an image forming apparatus according to a second embodiment of the present disclosure.

FIG. 15 illustrates an exemplary configuration of an image forming apparatus according to a second embodiment of the present disclosure. An image forming apparatus 100B illustrated in FIG. 15 differs from the image forming apparatus 100A described with reference to FIG. 1 in that the image forming apparatus 100B includes an imaging device 140B in place of the imaging device 140A. Similarly to the first embodiment, an illumination device 120A illuminates a subject 200 with a linearly polarized light beam or an unpolarized light beam, and the imaging device 140B captures an image of the subject 200 being illuminated with the light beam (linearly polarized light beam or unpolarized light beam) from the illumination device 120A.

The imaging device 140B includes an image sensor 142B having an imaging surface 142s and a housing 149B that houses the image sensor 142B. The imaging surface 142s of the image sensor 142B includes a first region Ra, a second region Rb, and a third region Rc. The first region Ra, the second region Rb, and the third region Rc are mutually different regions of the imaging surface 142s.

The housing 149B includes a plurality of apertures. In this example, three apertures APa, APb, and APc are provided in the housing 149B. The apertures APa, APb, and APc are formed in the surface that opposes the subject 200 at the time of imaging. Analyzers 146a, 146b, and 146c are disposed at the positions of the apertures APa, APb, and APc, respectively. It is not necessary that the positions of the analyzers 146a, 146b, and 146c precisely match the positions of the apertures APa, APb, and APc in an optical path connecting the subject 200 and the image sensor 142B, and the analyzers 146a, 146b, and 146c may be located, for example, in the vicinity of the apertures APa, APb, and APc and inside the housing 149B. The directions of the transmission axes of the analyzers 146a, 146b, and 146c are 0°, 60°, and 120°, respectively, as in the first embodiment.

In the configuration illustrated in FIG. 15, an objective lens 148a is disposed between the analyzer 146a and the image sensor 142B. In addition, objective lenses 148b and 148c are disposed, respectively, between the analyzer 146b and the image sensor 142B and between the analyzer 146c (not illustrated in FIG. 15) and the image sensor 142B. In this example, the distance between the objective lens 148a and the image sensor 142B is smaller than the distance between the analyzer 146a and the image sensor 142B. However, the arrangement of the analyzer 146a and the objective lens 148a is not limited to this example. It suffices that the objective lens 148a be located in an optical path connecting the subject 200 and the first region Ra, and the distance between the analyzer 146a and the image sensor 142B may be smaller than the distance between the objective lens 148a and the image sensor 142B, for example. The same applies to the objective lenses 148b and 148c, and it suffices that the objective lenses 148b and 148c be located, respectively, in an optical path connecting the subject 200 and the second region Rb and in an optical path connecting the subject 200 and the third region Rc.

The objective lens 148a images, of the returning light beams (reflection light beams) from the subject 200, the light beam that has passed through the analyzer 146a onto the first region Ra of the imaging surface 142s. In a similar manner, the objective lens 148b images, of the returning light beams from the subject 200, the light beam that has passed through the analyzer 146b onto the second region Rb of the imaging surface 142s, and the objective lens 148c images the light beam that has passed through the analyzer 146c onto the third region Rc of the imaging surface 142s. The first region Ra, the second region Rb, and the third region Rc of the imaging surface 142s can be said to be a portion that receives a component, of the returning light beams from the subject 200, having a polarization direction of 0°, a portion that receives a component having a polarization direction of 60°, and a portion that receives a component having a polarization direction of 120°, respectively. In the configuration illustrated in FIG. 15, the apertures APa to APc, the analyzers 146a to 146c, and the objective lenses 148a to 148c may have the functions similar to that of the beam splitter 144A in the configuration illustrated in FIG. 1 and may be collectively referred to as a beam splitter.

Figure 16:
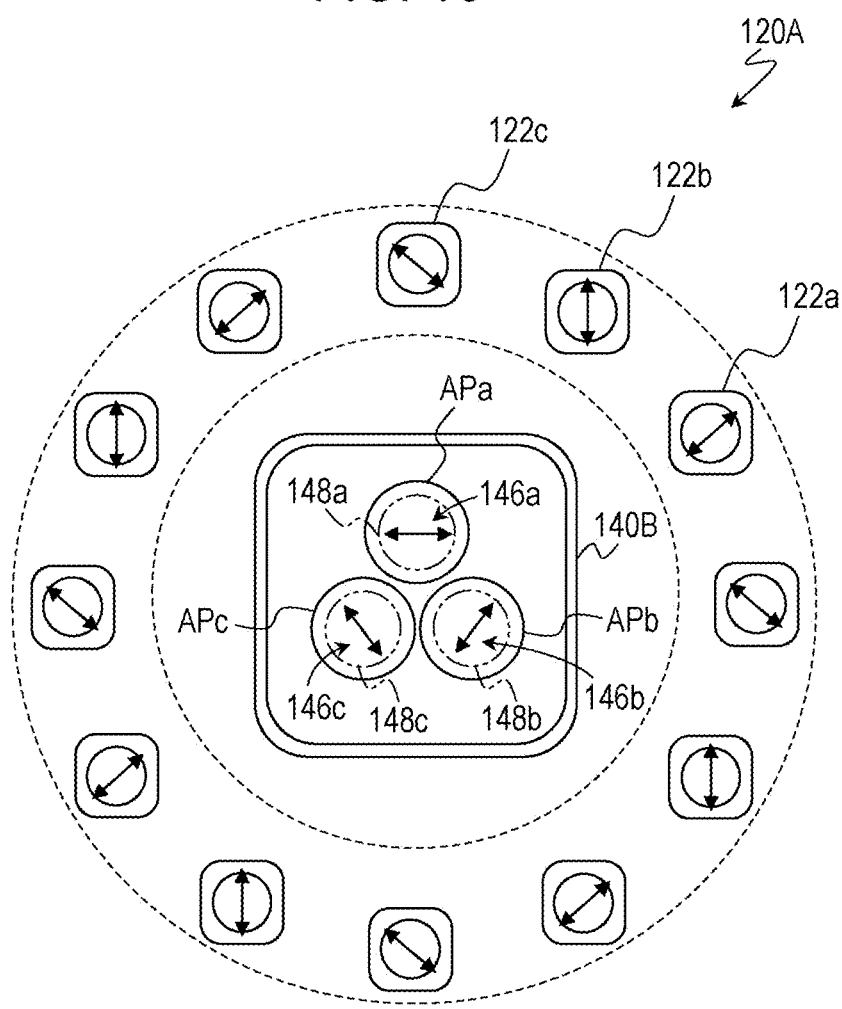
FIG. 16 illustrates a typical example of the arrangement of an illumination device and an imaging device in an image forming apparatus as viewed from a subject.

FIG. 16 illustrates a typical example of the arrangement of the illumination device 120A and the imaging device 140B in the image forming apparatus 100B as viewed from the subject 200. In FIG. 16, the thick double-headed arrows illustrated at the positions of the apertures APa, APb, and APc indicate the directions of the transmission axes of the analyzers 146a, 146b, and 146c, respectively.

Typically, a plane that includes emitters 122a to 122c in the illumination device 120A and a plane that includes the apertures APa to APc in the imaging device 140B are parallel to each other. FIG. 16 illustrates the illumination device 120A and the imaging device 140B as viewed from the subject 200 along the direction normal to the plane that includes the apertures APa to APc in the imaging device 140B. In the configuration illustrated in FIG. 16, the emitters 122a to 122c in the illumination device 120A surround the apertures APa to APc in the imaging device 140B as viewed from the subject 200 along the stated normal direction. In the second embodiment as well, the illumination device 120A may be driven in a similar manner to the first embodiment. In other words, the light sources 124 of the emitters 122a, the light sources 124 of the emitters 122b, and the light sources 124 of the emitters 122c (refer to FIG. 15) are turned on successively or simultaneously.

In this example, the apertures APa, APb, and APc are disposed in proximity to one another at substantially the center of the emitters 122a to 122c disposed in a ring shape, and the respective centers of the apertures APa, APb, and APc are located at the vertices of a right triangle. The distance between the centers of two adjacent apertures is, for example, approximately no less than 1.0 mm nor more than 10 mm. It is not essential that the respective centers of the apertures APa, APb, and APc be located at the vertices of a right triangle, and the respective centers of the apertures APa, APb, and APc may be located, for example, at the vertices of a desired triangle or at three vertices selected from the plurality of vertices of another figure such as a square.

As schematically illustrated in FIG. 15, in the imaging device 140B, a light beam coming from a given point on the subject 200 and passing through the analyzer 146a, a light beam coming from the same point and passing through the analyzer 146b, and a light coming from the same point and passing through the analyzer 146c are imaged at mutually different positions on the imaging surface 142s. Therefore, similarly to the imaging device 140A according to the first embodiment, with the imaging device 140B, polarization images C0, C60, and C120 that are based on the light beams of which the polarization directions of the incident light beams differ from one another by 60° can be acquired in a single instance of imaging. However, since the positions of the apertures APa, APb, and APc differ from one another, a parallax is produced among the acquired polarization images C0, C60, and C120. Therefore, an image forming circuit 164 that has received an output from the image sensor 142B executes correction processing of cancelling the parallax among the plurality of polarization images.

Figure 17:
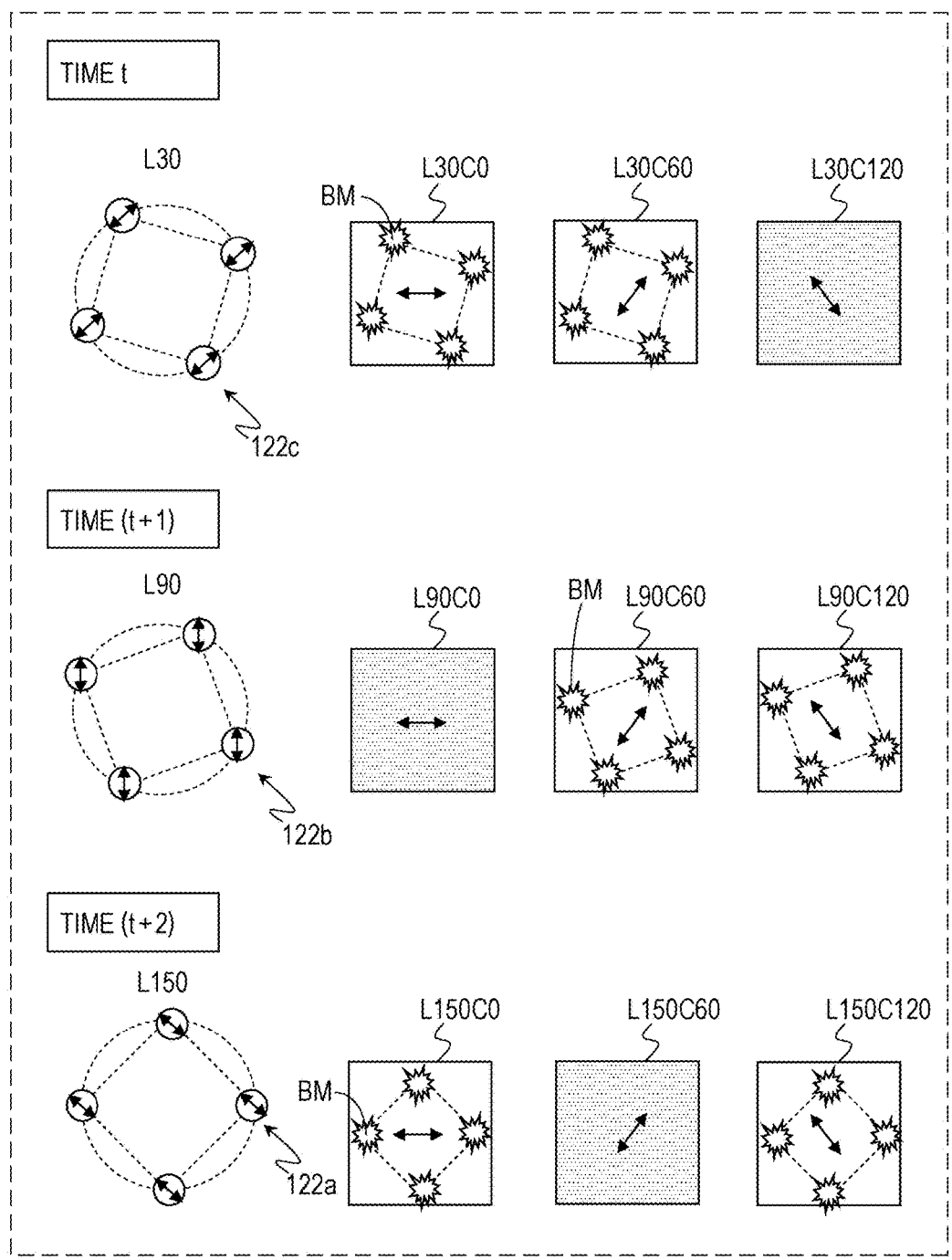
FIG. 17 is an illustration for describing an example of processing for cancelling the parallax among polarization images.

FIG. 17 is an illustration for describing an example of the processing for cancelling the parallax among the polarization images. In FIG. 17, the operating state of the illumination device 120A is schematically illustrated in the leftmost column. To the right of the operating state of the illumination device 120A, three polarization images acquired at the same timing in accordance with the operating state are illustrated.

As have been described above, linearly polarized light beams are emitted successively from the plurality of emitters 122a, the plurality of emitters 122b, and the plurality of emitters 122c in the first mode. Herein, linearly polarized light beams are emitted from four emitters 122a at a given timing (time t), and imaging is executed. At this point, as illustrated in the uppermost row in FIG. 17, a polarization image L30C0 based on a light beam that has passed through the analyzer 146a, a polarization image L30C60 based on a light beam that has passed through the analyzer 146b, and a polarization image L30C120 based on a light beam that has passed through the analyzer 146c are acquired by the imaging device 140B. In addition, linearly polarized light beams are emitted from four emitters 122b at another given timing (time (t+1)), and imaging is executed. Thus, in a similar manner, three polarization images L90C0, L90C60, and L90C120 based on light beams that have passed through the analyzer 146a, the analyzer 146b, and the analyzer 146c, respectively, are acquired. Furthermore, linearly polarized light beams are emitted from four emitters 122c at yet another given timing (time (t+2)), and imaging is executed. Thus, three polarization images L150C0, L150C60, and L150C120 are acquired.

Herein, similarly to the first embodiment, a human eyeball is illustrated as an example of the subject 200. When a subject having a transparent or semi-transparent and smooth surface, such as a human eyeball, is irradiated with linearly polarized light beams PL from a plurality of positions as schematically illustrated in FIG. 15, a plurality of bright spots BP resulting from the specular reflection appear on the subject 200. The positions of these bright spots BP reflect the positions of the light sources 124 that are being turned on at the time of imaging.

Referring to FIG. 17, the light sources 124 of the four emitters 122a are turned on at the time t. Herein, the centers of the four emitters 122a are located at the vertices of a square. Therefore, as schematically illustrated in FIG. 17, in the polarization images L30C0, L30C60, and L30C120 acquired at this time, images BM of the four bright spots BP appear except in the polarization image L30C120 that is a crossed-Nicols image.

The polarization images L30C0, L30C60, and L30C120 are images acquired from mutually different viewpoints, and a parallax is present among these images. However, the positional relationship among the four images BM in the polarization image L30C0 is identical to the positional relationship among the four images BM in the polarization image L30C60. For example, when the subject 200 is irradiated straight with the linearly polarized light beam PL, and imaging is executed, a square is drawn by connecting the centers of the respective four images BM in the polarization image L30C0, and a similar square is drawn by connecting the centers of the respective four images BM in the polarization image L30C60. As will be described hereinafter, an influence of the difference in the viewpoint at the time of imaging can be cancelled by detecting the positions of the images BM in the polarization images and by translating these polarization images or carrying out other image processing such that the images BM are superposed on each other between the two polarization images.

For example, the image forming circuit 164 detects the four images BM in the polarization image L30C0 and the four images BM in the polarization image L30C60 and obtains the coordinates of these images BM. The coordinates of each of the images BM can be obtained in the form of the coordinates of the pixel located at the center among a plurality of pixels having pixel values greater than a threshold value set in advance. The distance between the coordinates of the corresponding images BM in the two images corresponds to the distance between the centers of the aperture APa and the aperture APb. Furthermore, the image forming circuit 164 translates the polarization images L30C0 and L30C60, for example, such that the coordinates of the corresponding images BM in the two images coincide with appropriate coordinates. With this operation, the parallax between the polarization images L30C0 and L30C60 is cancelled.

The parallax between the polarization images L30C60 and L30C120 can be estimated from the parallax between the polarization images L90C60 and L90C120 acquired at the time (t+1). As illustrated in the middle row of FIG. 17, of the polarization images L90C0, L90C60, and L90C120, in the polarization images L90C60 and L90C120, the images BM appear at the positions corresponding to the arrangement of the emitters 122b of which the light sources 124 are being turned on at the time of imaging. Through a similar procedure, the parallax between the polarization images L90C60 and L90C120 can be cancelled by translating these images such that the coordinates of the corresponding images BM in the polarization images L90C60 and L90C120 coincide with appropriate coordinates.

The polarization images L90C60 and L90C120 are images acquired with the apertures APb and APc, respectively, serving as the viewpoints, and the polarization images L30C60 and L30C120 acquired at the time t are also images acquired with the apertures APb and APc, respectively, serving as the viewpoints. Therefore, the parallax between the polarization images L90C60 and L90C120 matches the parallax between the polarization images L30C60 and L30C120. Accordingly, the parallax between the polarization images L30C60 and L30C120 can be cancelled by translating the polarization image L30C60 by the same amount and in the same direction as the polarization image L90C60 and by translating the polarization image L30C120 by the same amount and in the same direction as the polarization image L90C120.

In a similar manner, the parallax between the polarization images L150C0 and L150C120, the parallax between the polarization images L30C0 and L30C120, and the parallax between the polarization images L90C0 and L90C120 can be obtained on the basis of the positions of the images BM that appear in the polarization images L150C0 and L150C120, and these parallaxes can be cancelled through translations or the like. In the end, the nine polarization images can be translated on the basis of the positions of the images BM such that an influence of the difference in the viewpoint at the time of imaging can be cancelled. When the parallaxes are cancelled in the nine polarization images, an averaged pseudo-parallel-Nicols image SPA and an averaged crossed-Nicols image OA can be formed on the basis of the polarization images in which the parallaxes are cancelled, and an image PD serving as an image of the subject 200 can be obtained on the basis of the difference between the averaged pseudo-parallel-Nicols image SPA and the averaged crossed-Nicols image OA. The image PD can be used advantageously to detect, for example, a foreign object, a flaw, or the like on a cornea. Typically, although the images BM of the bright spots BP remain in the image PD, the presence of the images BM of the bright spots BP rarely pose a large problem in observing the cornea. In FIG. 17, the images BM of the bright spots BP are merely exaggerated and enlarged for the purpose of description.

The magnitude of the parallax associated with the difference in the viewpoint at the time of imaging can be found through the principle described above if the second mode is executed after the first mode is executed, and thus the parallax among the polarization images NC0, NC60, and NC120 acquired in the second mode can be cancelled. Processing (e.g., rotational movement) other than the translation may be executed, as necessary, in place of the translation or in addition to the translation on the basis of the pattern of the images BM of the bright spots BP that appear in the polarization images.

According to the second embodiment, three polarization images from three viewpoints can be obtained at once through a single instance of imaging. Furthermore, as the imaging is executed a plurality of times with the polarization direction of the illumination light beam being varied, the parallax among the plurality of polarization images can be cancelled on the basis of the positions of the images of the bright spots in the polarization images that appear at the positions corresponding to the arrangement of the light sources that are being turned on at the time of imaging. In the example described with reference to FIG. 17, the centers of the four emitters of which the light sources 124 are turned on at the same timing are located at the vertices of a square. However, it is not necessary that the plurality of emitters 122 that are turned on at the same timing be located at the vertices of a square, a regular polygon, or the like. As is apparent from the processing of cancelling the parallax described above, a desired arrangement can be applied to the arrangement of the plurality of emitters 122. Although the coordinates of the images BM in the polarization images are used herein, the plurality of polarization images may be subjected to processing such as translation such that the coordinates of the centers of gravity of figures obtained by connecting the positions of the images BM in the respective polarization images coincide with one another, for example.

Modification of Second Embodiment

Figure 18:
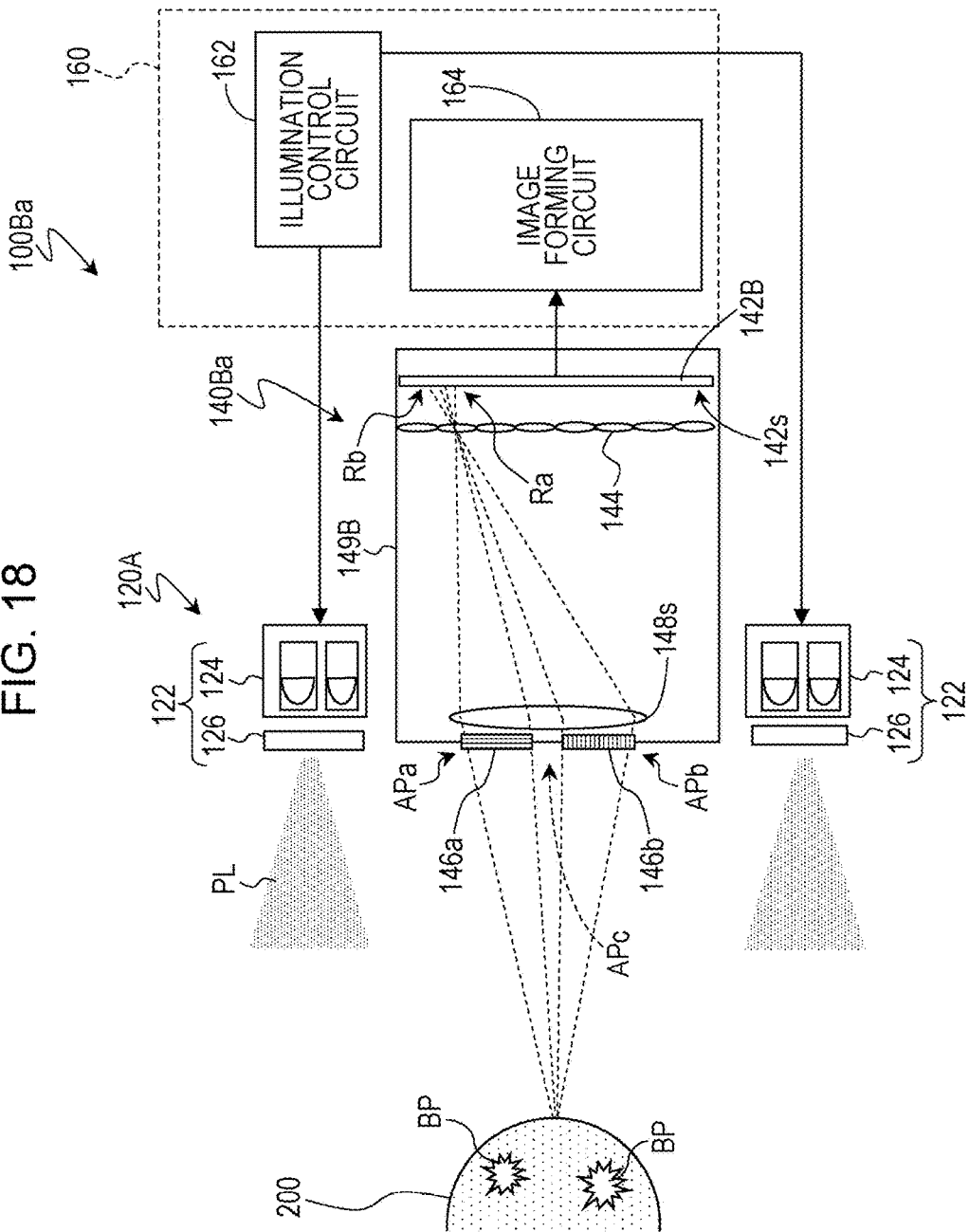
FIG. 18 illustrates a modification of an image forming apparatus according to the second embodiment of the present disclosure.

FIG. 18 illustrates a modification of an image forming apparatus according to the second embodiment of the present disclosure. An image forming apparatus 100Ba illustrated in FIG. 18 has a configuration in which the imaging device 140B illustrated in FIG. 15 is replaced with an imaging device 140Ba. As compared to the imaging device 140B, the imaging device 140Ba includes, in place of the objective lenses 148a to 148c, an objective lens 148s disposed between the apertures APa, APb, and APc and the image sensor 142B. The objective lens 148s may be disposed in either of the front side and the back side of the analyzers 146a to 146c. The imaging device 140Ba further includes a microlens array 144 disposed between the objective lens 148s and the imaging surface 142s of the image sensor 142B. The microlens array 144 includes a plurality of microlenses that oppose respective imaging cells of the image sensor 142B.

In this example, all of the light beam that has passed through the analyzer 146a disposed at the aperture APa, the light beam that has passed through the analyzer 146b disposed at the aperture APb, and the light beam that has passed through he analyzer 146c disposed at the aperture APc pass through the objective lens 148s. However, since the microlens array 144 is disposed in front of the imaging surface 142s of the image sensor 142B, the light beam that has passed through the aperture APa, the light beam that has passed through the aperture APb, and the light beam that has passed through the aperture APc reach different regions Ra, Rb, and Rc, respectively, of the imaging surface 142s. The optical system of the imaging device 140Ba may be designed, for example, such that the light beam that has passed through the aperture APa, the light beam that has passed through the aperture APb, and the light beam that has passed through the aperture APc are imaged on the imaging cells in mutually different rows (or columns) of the arrays of the imaging cells. In other words, in this case, returning light beams from the subject 200 reach mutually different regions of the imaging surface 142s in accordance with the vibration directions of the electric field vectors, and a signal of an image in which three polarization images having parallaxes are interleaved is output from the imaging device 140Ba.

As the output signal is split into signals of the three polarization images through image processing in a later stage, the three polarization images having the parallaxes corresponding to the directions of the transmission axes of the analyzers 146a to 146c can be obtained. The image forming apparatus 100Ba can be driven in a similar manner to the image forming apparatus 100B described with reference to FIG. 15, and processing similar to that of the image forming apparatus 100B can be applied to the acquired polarization images.

Third Embodiment

Figure 19:
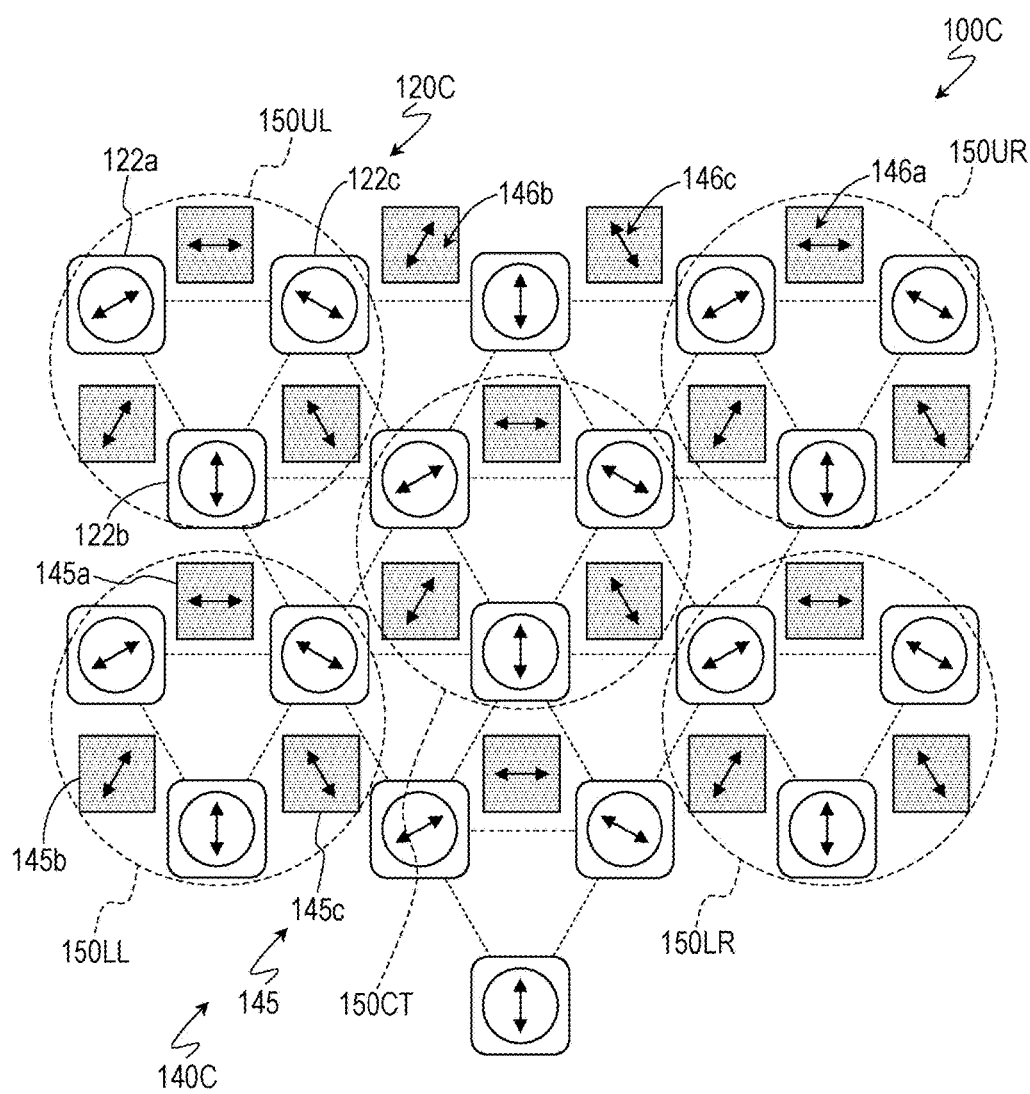
FIG. 19 illustrates a part of an exemplary configuration of an image forming apparatus according to a third embodiment of the present disclosure.

FIG. 19 illustrates a part of an exemplary configuration of an image forming apparatus according to a third embodiment of the present disclosure. An image forming apparatus 100C illustrated in FIG. 19 includes an illumination device 120C that includes a plurality of emitters 122, an imaging device 140C, and a control circuit (not illustrated). The illumination device 120C includes the plurality of emitters 122, and the imaging device 140C includes a plurality of polarization cameras 145. The plurality of polarization cameras 145 include polarization cameras 145a to 145c. The control circuit in the image forming apparatus 100C may include an illumination control circuit and an image forming circuit similar to those in the image forming apparatus 100A described above.

FIG. 19 illustrates an example of the arrangement of emitters 122a to 122c and the polarization cameras 145a to 145c in the image forming apparatus 100C. In the example illustrated in FIG. 19, the emitters 122a to 122c and the polarization cameras 145a to 145c are disposed within the same plane. FIG. 19 illustrates a typical arrangement of the emitters 122a to 122c and the polarization cameras 145a to 145c as viewed from the subject along the direction normal to the plane in which the emitters 122a to 122c and the polarization cameras 145a to 145c are disposed.

In this example, each of the polarization cameras 145a to 145c includes an image sensor, an analyzer, and an objective lens and acquires a polarization image of the subject that is based on a light beam having a specific polarization direction. The polarization cameras 145a, 145b, and 145c include analyzers 146a, 146b, and 146c, respectively. In FIG. 19, the double-headed arrows illustrated over the shaded rectangles indicate the directions of the transmission axes of the respective analyzers. The directions of the transmission axes of the analyzers 146a, 146b, and 146c are 0°, 60°, and 120°, similarly to the examples described thus far. As schematically illustrated in FIG. 19, the directions of the transmission axes of the polarizers in the emitters 122a, 122b, and 122c are similar to those in the examples described thus far and are 30°, 90°, and 150°, respectively.

As schematically illustrated in FIG. 19, the emitters 122a to 122c are disposed such that their centers are located on the lattice points of a triangular lattice. In this example, the polarization cameras 145a to 145c are also disposed such that their centers are located on the lattice points of a triangular lattice, and each polarization camera is located at the center of a triangle formed by the emitters 122a, 122b, and 122c that are adjacent to one another. The image forming apparatus 100C includes a plurality of unit structures that each include the emitters 122a to 122c and the polarization cameras 145a to 145c. The dashed circles illustrated in FIG. 19 indicate five unit structures 150CT, 150UL, 150UR, 150LL, and 150LR. The image forming apparatus 100C has a structure in which a plurality of unit structures are tiled.

Figure 20:
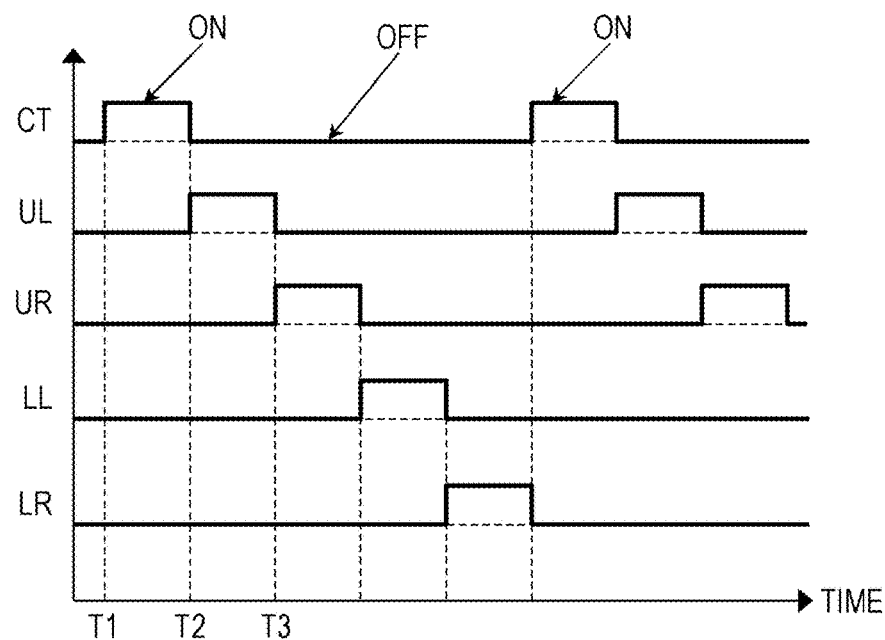
FIG. 20 illustrates an example of drive timings of light sources of emitters in unit structures.

In one operation example of the image forming apparatus 100C, the illumination control circuit and the image forming circuit of the control circuit in the image forming apparatus 100C select one of the plurality of unit structures and drive the unit structures successively. FIG. 20 illustrates an example of the drive timings of the light sources of the emitters 122a to 122c in the unit structures 150CT, 150UL, 150UR, 150LL, and 150LR.

In the example illustrated in FIG. 20, the emitters 122a to 122c and the polarization cameras 145a to 145c in the unit structure 150CT among the five unit structures are driven from the time T1 to the time T2. As will be described later, at this point, the unit structure 150CT is driven, for example, successively in the first mode and then in the second mode, and a plurality of polarization images of the subject are acquired with the polarization cameras 145a to 145c. As illustrated in FIG. 20, the light sources of the emitters 122a to 122c in the unit structures 150UL, 150UR, 150LL, and 150LR are all in the OFF state from the time T1 to the time T2. Next, at the time T2, the light sources of the emitters 122a to 122c in the unit structure 150CT are turned OFF, and the light sources of the emitters 122a to 122c in the unit structure 150UL are turned ON. In other words, from the time T2 to the time T3, the emitters 122a to 122c and the polarization cameras 145a to 145c in the unit structure 150UL are driven, and a plurality of polarization images of the subject are acquired with the polarization cameras 145a to 145c in the unit structure 150UL. Thereafter, in a similar manner, a plurality of polarization images of the subject are acquired successively with the polarization cameras in the unit structures 150UR, 150LL, and 150LR. As illustrated in FIG. 20, the cycle of acquiring polarization images with the unit structures 150CT, 150UL, 150UR, 150LL, and 150LR may be repeated a plurality of times.

Figure 21:
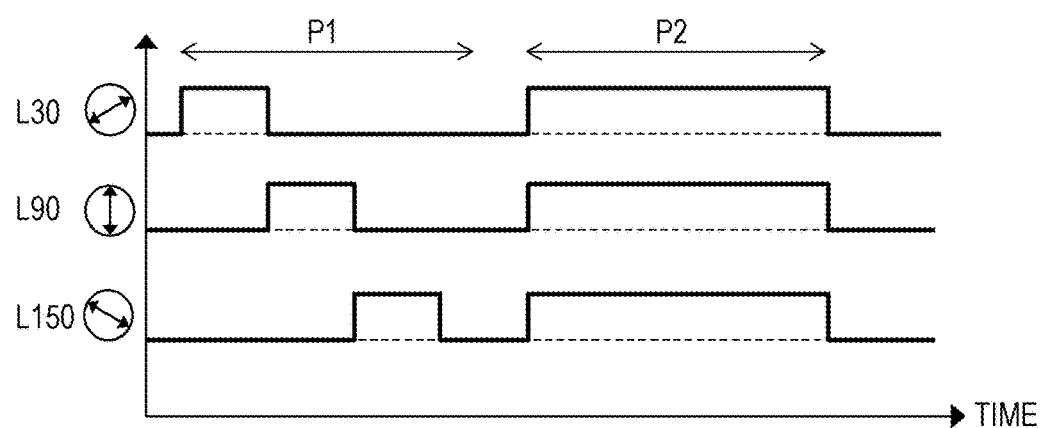
FIG. 21 illustrates a typical example of lighting timings of the light sources of the emitters in each unit structure.

FIG. 21 illustrates the lighting timings of the light sources of the emitters 122a and 122c in each unit structure. The double-headed arrow P1 illustrated in FIG. 21 represents the operation period in the first mode, and the double-headed arrow P2 represents the operation period in the second mode. As illustrated in FIG. 21, in the period P1, the light sources of the emitters 122a, the light sources of the emitters 122b, and the light sources of the emitters 122c are selectively and successively turned on, and three polarization images are acquired with the polarization cameras 145a to 145c during each period in which a given set of light sources is ON. Thus, a total of nine polarization images are acquired. In the period P2, the light sources of the emitters 122a, the light sources of the emitters 122b, and the light sources of the emitters 122c are turned on simultaneously, and three polarization images are acquired with the polarization cameras 145a to 145c. This set of three polarization images may be acquired a plurality of times in the period P2.

In this manner, in the embodiment described herein, imaging is executed successively in the plurality of unit structures, and thus an image of the subject can be obtained with each of the unit structures. As will be described hereinafter, the image forming apparatus 100C can be used advantageously to observe an organism, for example.

Figure 22:
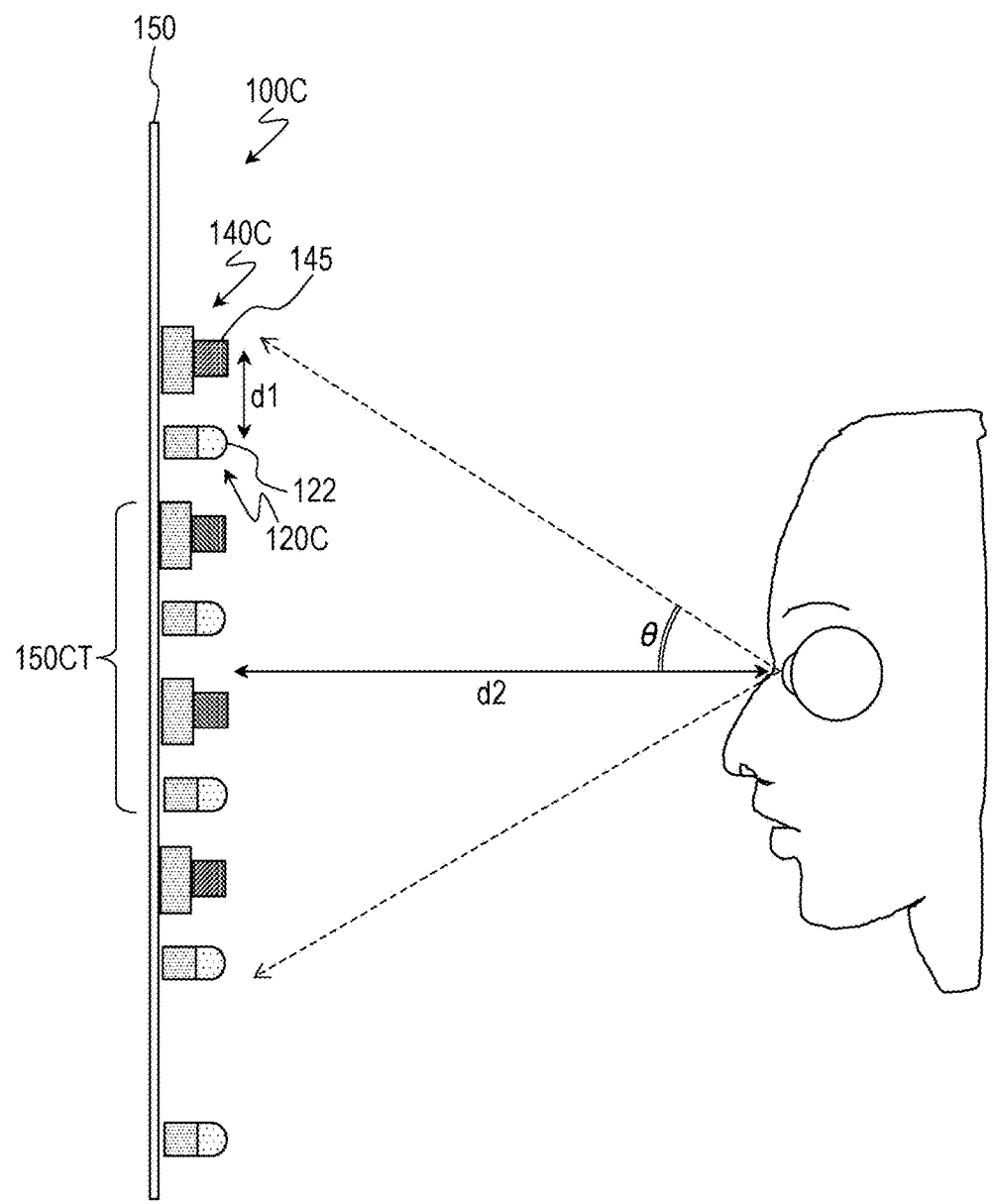
FIG. 22 illustrates the arrangement of an illumination device and an imaging device with respect to a subject.

FIG. 22 illustrates the arrangement of the illumination device 120C and the imaging device 140C with respect to the subject. In the example illustrated in FIG. 22, the plurality of emitters 122 and the plurality of polarization cameras 145 in the image forming apparatus 100C are disposed on one principal surface (hereinafter, may be referred to as a "sensor surface" for the purpose of description) of a substrate 150 (e.g., circuit board). For example, when an image of a human eyeball is to be captured, the illumination device 120C and the imaging device 140C are disposed such that the plurality of emitters 122 and the plurality of polarization cameras 145 on the substrate 150 oppose the face. At the time of imaging, the arrangement of the plurality of emitters 122 and the plurality of polarization cameras 145 with respect to the subject is adjusted such that the center of the eyeball serving as the subject is located on the line normal to the center of the substrate 150.

As illustrated in FIG. 22, when the illumination device 120C and the imaging device 140C are viewed from a side, the distance d2 between the sensor surface and the surface of the eyeball is typically 20 times or more of the distance d1, in which d1 is the distance between the center of a given emitter 122 and the center of the objective lens of the polarization camera 145 that is closest to the given emitter 122. As shown clearly in FIG. 19, the plurality of emitters 122 and the plurality of polarization cameras 145 are disposed so as to be substantially evenly distributed two-dimensionally (in a plane or in a curve) and cover the range of, for example, up to θ=45° in the vertical and horizontal directions, which is the movable range of a human eyeball. Herein, θ is an angle formed by a line segment connecting the center of the unit structure 150CT and the center of the eyeball and a line segment connecting a polarization camera 145 of interest and the center of the eyeball.

The unit structures 150CT, 150UL, 150UR, 150LL, and 150LR correspond to the regions of the sensor surface when the subject looks to the center, the upper left, the upper right, the lower left, and the lower right, respectively. Each of the unit structures includes the emitters 122a, 122b, and 122c in which the angles of the transmission axes of the polarizers are 30°, 90°, and 120°, respectively, and includes the polarization cameras 145a, 145b, and 145c in which the angles of the transmission axes of the analyzers are 0°, 60°, and 150°, respectively. In other words, an operation and processing similar to those of the image forming apparatus 100B according to the second embodiment can be applied to each of the unit structures 150CT, 150UL, 150UR, 150LL, and 150LR. In the example described herein, the unit structures 150CT, 150UL, 150UR, 150LL, and 150LR are disposed two-dimensionally, and the arrangement thereof is symmetric. Thus, an image of the cornea or the retina of the eyeball can be captured with certainty even if the eyeball moves. When an existing optical device for eye examination is used, the head is fixed with a belt, and the observation needs to be carried out in a state in which the subject refrains from moving his/her eyes as much as possible. In contrast, according to the third embodiment, such a constraint can be reduced, and the stress on the subject can be reduced accordingly. In addition, unlike an eye wearable sensor or the like of an eyeglass type or a contact lens type, information on the state of the eyeball can be acquired contactlessly through imaging.

In the example illustrated in FIG. 21, the first mode and the second mode are executed continually in a single unit structure. A given unit structure may acquire polarization images in a period between when another given unit structure executes the first mode and when this given unit structure executes the second mode. However, an operation in which the first mode and the second mode are executed without an interval in a single unit structure is less likely to be affected by the movement of the eyeball and is thus advantageous in the observation of the eyeball. In the diagnosis of glaucoma, for example, ophthalmotonometry is carried out. In the ophthalmotonometry, a deformation of the cornea is examined in a state in which the air is blown against the cornea. With the use of the image forming apparatus 100C, the observation of the surface of the cornea and the measurement of the deformation of the cornea caused by the air jet can be executed successively in the first and second modes.

As can be seen from FIG. 22 as well, the positions of the polarization cameras 145a, 145b, and 145c on the sensor surface in each unit structure differ from one another. In other words, a parallax is present among the polarization images acquired by the polarization cameras 145a, 145b, and 145c. An influence of the parallax among the polarization images can be cancelled, for example, through the translation or the like that uses the coordinates of the images BM of the bright spots appearing in the polarization images in a similar manner to the second embodiment as described with reference to FIG. 17. When the translation is applied to the polarization images, a blank region in which the data of the subject is not present may appear in the translated images. However, since the unit structures 150CT, 150UL, 150UR, 150LL, and 150LR are disposed two-dimensionally herein, an effect similar to that of the case in which the images of the subject are captured from a plurality of directions with the use of the image forming apparatus 100B according to the second embodiment can be obtained. To rephrase, as the number of viewpoints at the time of imaging increases, the field of view is enlarged, and a blank region generated in the polarization images acquired by the unit structure 150CT, for example, can be interpolated with the use of the data of the polarization images acquired by another unit structure 150UL, 150UR, 150LL, or 150LR. Although a configuration in which each of the polarization cameras 145a, 145b, and 145c separately includes an image sensor is illustrated as an example, a configuration similar to that of the imaging device 140B or 140Ba of the second embodiment may be applied to the polarization camera 145 in each unit structure.

Figure 23:
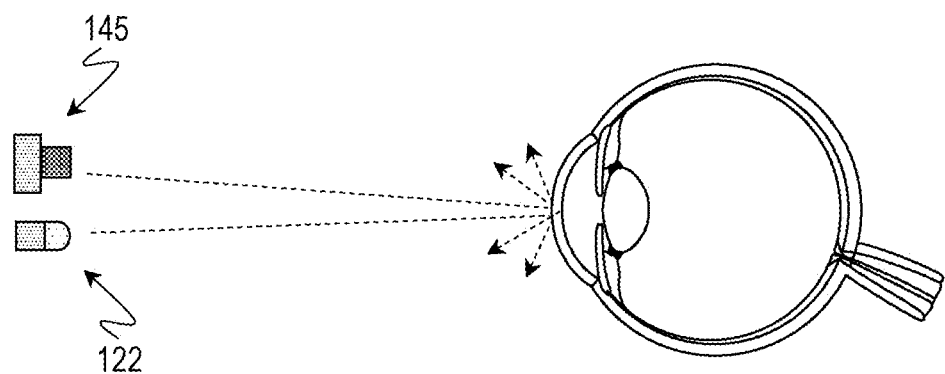
FIG. 23 is an illustration for describing an effect obtained through imaging by a unit structure and schematically illustrates a relationship between an illumination light beam and a returning light beam in a first mode.
Figure 24:
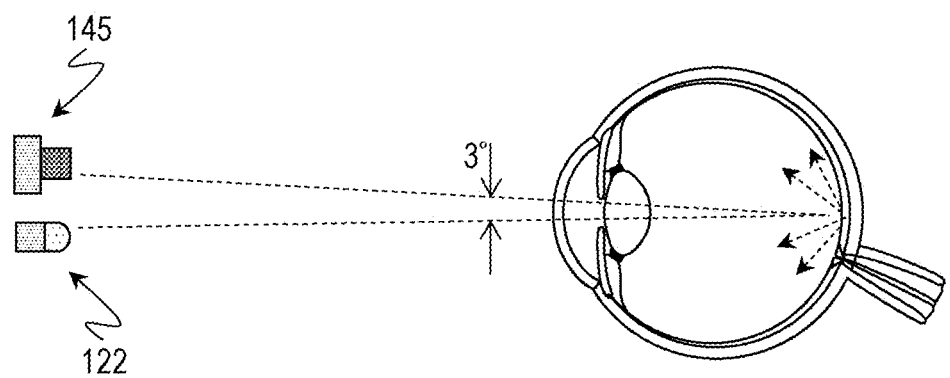
FIG. 24 is an illustration for describing an effect obtained through imaging by a unit structure and schematically illustrates a relationship between an illumination light beam and a returning light beam in a second mode.

FIGS. 23 and 24 are illustrations for describing the effect obtained through the imaging with the unit structure 150CT. FIG. 23 schematically illustrates the relationship between an illumination light beam and a returning light beam in the first mode, and FIG. 24 schematically illustrates the relationship between an illumination light beam and a returning light beam in the second mode.

The unit structure 150CT is located in the vicinity of the center of the sensor surface, and the emitters 122a to 122c are all located in the vicinity of the three polarization cameras 145 in the unit structure 150CT, as illustrated in FIG. 19. When the distance d2 between the sensor surface and the surface of the eyeball (refer to FIG. 22) is 200 mm, which is the standard distance of distinct vision, d1 is, for example, 10 mm. With such an arrangement, as tan 3° is approximately 0.05 (=1/20), θ is approximately 3°, and a state close to coaxial illumination is achieved.

Under such illumination, as the imaging in the first mode is executed, the concavities and convexities (e.g., flaw) in the surface of the cornea can be detected on the basis of the light beam reflected at the vicinity of the surface of the cornea, as schematically illustrated in FIG. 23. In addition, the arrangement in which θ is reduced to approximately 3° achieves a geometric arrangement with which the fundus can be imaged. Therefore, with the second mode, a light beam can be advanced to the vicinity of the fundus, and the returning light beam can be observed, as schematically illustrated in FIG. 24. In other words, the pupil can be imaged brightly. This means that information on the polarization state of a light beam that is scattered by the fundus and that emerges through the cornea into the air can be acquired through imaging. Therefore, according to an embodiment of the present disclosure, on the basis of the acquired images, information on the direction normal to the surface of a portion of the cornea that corresponds to the pupil, or in other words, information on the shape of the portion of the cornea that corresponds to the pupil can be acquired, or the presence of any lesion in the retina of the fundus can be diagnosed.

Figure 25:
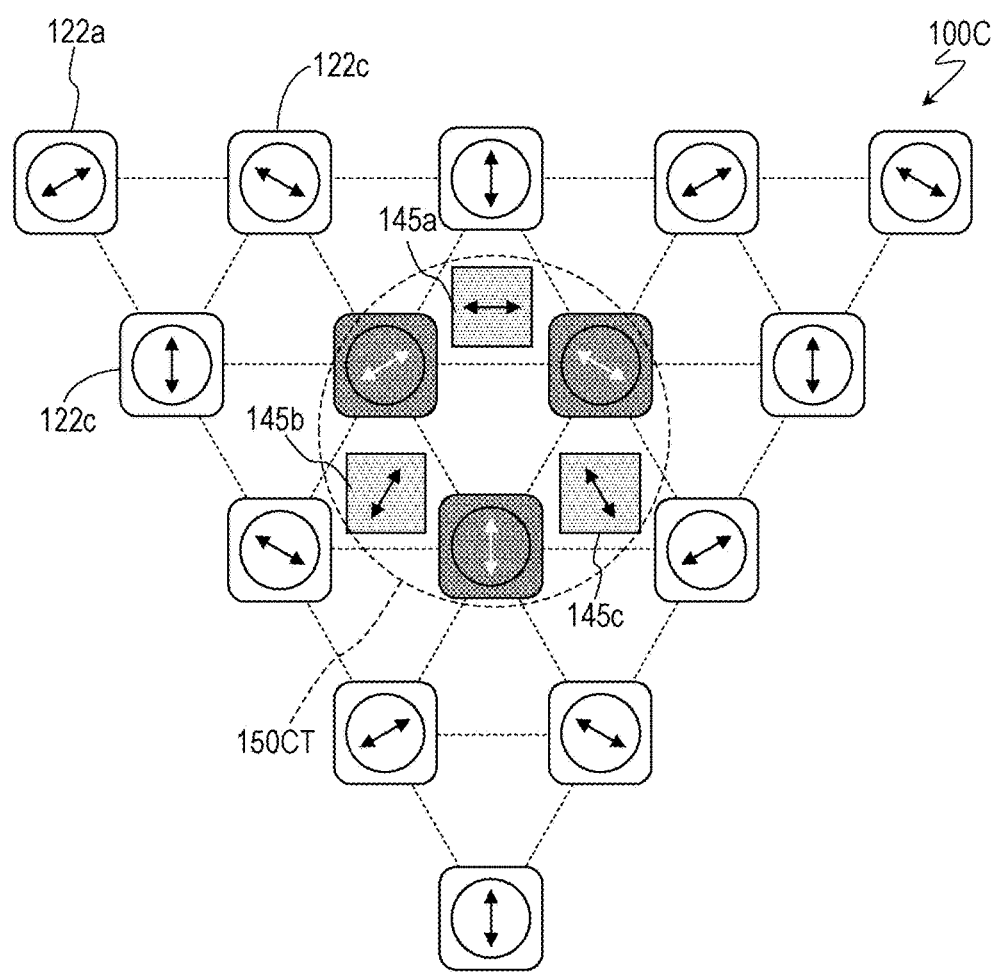
FIG. 25 is an illustration for describing an application example of operations of an illumination device and an imaging device.

FIG. 25 illustrates an application example of the operations of the illumination device 120C and the imaging device 140C. In the example illustrated in FIG. 25, polarization images of the subject are acquired with the polarization cameras 145a to 145c in the unit structure 150CT in a state in which the light sources of the emitters 122a to 122c included in the unit structure 150CT are turned OFF and the light sources of the emitters 122a to 122c surrounding the unit structure 150CT are turned ON.

Figure 26:
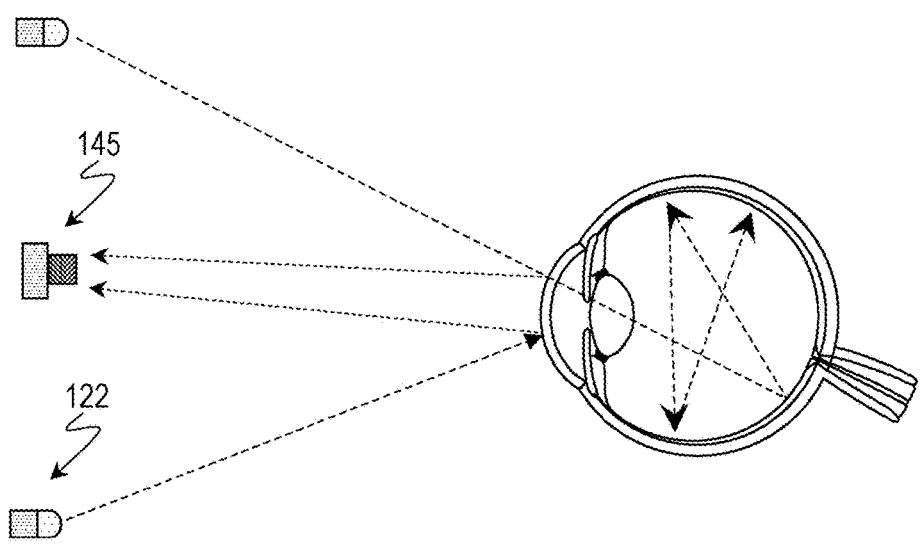
FIG. 26 is an illustration for describing an effect obtained through the operations illustrated in FIG. 25.

FIG. 26 is an illustration for describing an effect obtained by the operations illustrated in FIG. 25. Under the illumination such as the one illustrated in FIG. 25, θ is equal to or greater than 3°, and the light beam that has entered the pupil is reflected and absorbed thereinside and does not emerge to the outside. Thus, a captured image of the pupil is dim, and a light beam primarily reflected at the cornea can selectively be made incident on the polarization camera 145. Therefore, in the first mode, the concavities and convexities (e.g., flaw) in the surface of the eyeball can be detected on the basis of the polarization images of a light beam reflected at the vicinity of the surface of the cornea. In addition, in the second mode, a specular reflection state can be achieved substantially across the entire cornea, and the polarization images useful for estimating the vector normal to the surface of the cornea can be acquired with higher certainty.

As described thus far, according to the embodiments of the present disclosure, an image that provides information useful for detecting a flaw or the like in the surface of an object having a transparent or semi-transparent and smooth surface and an image that provides information useful for measuring the shape of the object can be acquired with a single apparatus without an additional piece of hardware being provided separately. In addition, a plurality of polarization directions of linearly polarized light beams illuminating the subject and a plurality of polarization directions of light beams incident on the image sensor are selected in a well-balanced manner, and thus an image with less deterioration in the image quality can be formed while an increase in the frequency of the imaging is suppressed. The extension to imaging from a plurality viewpoints is relatively easy, and an image forming apparatus according to an embodiment of the present disclosure can be used, for example, as a camera for observing eyes contactlessly.

An embodiment of the present disclosure can be used to detect a foreign object on a transparent object or the condition (concavities and convexities, flaw, etc.) of the surface of a transparent object. In addition, an embodiment can be used to measure the shape of a transparent object. An image forming apparatus according to the present disclosure is particularly useful for contactless sensing of an eyeball of an organism, and an image forming apparatus according to the present disclosure can be applied to grasping the health condition of a human, an animal (livestock, pet), and the like and to detecting the abnormality of the cornea.

What is claimed is:

1. An image forming apparatus, comprising:
one or more first emitters, one or more second emitters, and one or more third emitters of an illumination device, the one or more first emitters each emitting a first light beam having a polarization direction of 30°, the one or more second emitters each emitting a second light beam having a polarization direction of 90°, the one or more third emitters each emitting a third light beam having a polarization direction of 150°, the illumination device illuminating a subject with at least one of the first, second, and third light beams;
a beam splitter that splits a returning light beam from the subject and outputs a first component having a polarization direction of 0°, a second component having a polarization direction of 60°, and a third component having a polarization direction of 120°;
an imaging surface of an imaging device that includes a first region that receives the first component, a second region that receives the second component, and a third region that receives the third component; and
an image forming circuit,
wherein the image forming circuit generates an image of the subject on the basis of:
a first group of images of the first component, the second component, and the third component acquired by the imaging device when the subject is illuminated with the first light beam among the first, second, and third light beams,
a second group of images of the first component, the second component, and the third component acquired by the imaging device when the subject is illuminated with the second light beam among the first, second, and third light beams, and
a third group of images of the first component, the second component, and the third component acquired by the imaging device when the subject is illuminated with the third light beam among the first, second, and third light beams.

2. The image forming apparatus according to claim 1, wherein the beam splitter includes
a prism, and
first, second, and third analyzers of which directions of transmission axes are 0°, 60°, and 120°, respectively.

3. The image forming apparatus according to claim 1, wherein the first group of images includes two first polarization images and one first crossed-Nicols image,
wherein the second group of images includes two second polarization images and one second crossed-Nicols image,
wherein the third group of images includes two third polarization images and one third crossed-Nicols image, and wherein the image forming circuit forms an averaged pseudo-parallel-Nicols image that is based on the two first polarization images, the two second polarization images, and the two third polarization images and an averaged crossed-Nicols image that is based on the one first crossed-Nicols image, the one second crossed-Nicols image, and the one third crossed-Nicols image, and forms an image of the subject by obtaining a difference between the averaged pseudo-parallel-Nicols image and the averaged crossed-Nicols image.

4. The image forming apparatus according to claim 1,
wherein the illumination device further illuminates the subject simultaneously with the first, second, and third light beams, and
wherein the imaging device
images each of a light beam incident on the first region, a light beam incident on the second region, and a light beam incident on the third region when the subject is illuminated with the first, second, and third light beams.

5. An image forming apparatus, comprising:
one or more first emitters, one or more second emitters, and one or more third emitters of an illumination device, the one or more first emitters each emitting a first light beam having a polarization direction of 30°, the one or more second emitters each emitting a second light beam having a polarization direction of 90°, the one or more third emitters each emitting a third light beam having a polarization direction of 150°, the illumination device illuminating a subject with at least one of the first, second, and third light beams;
a housing of an imaging device having first, second, and third apertures provided therein, and an image sensor having an imaging surface;
one or more objective lenses located between the subject and the imaging surface;
a first analyzer that is disposed at a position of the first aperture and of which a direction of a transmission axis is 0°;
a second analyzer that is disposed at a position of the second aperture and of which a direction of a transmission axis is 60°;
a third analyzer that is disposed at a position of the third aperture and of which a direction of a transmission axis is 120°; and
an image forming circuit,
wherein the imaging surface of the imaging device includes a first region, a second region, and a third region, the first region receiving a fourth light beam, of a returning light beam from the subject, that has passed through the first analyzer, the second region receiving a fifth light beam, of the returning light beam from the subject, that has passed through the second analyzer, the third region receiving a sixth light beam, of the returning light beam from the subject, that has passed through the third analyzer, and
wherein the image forming circuit generates an image of the subject on the basis of:
  a first group of images of the fourth, fifth, and sixth light beams acquired by the imaging device when the subject is illuminated with the first light beam among the first, second, and third light beams,
  a second group of images of the fourth, fifth, and sixth light beams acquired by the imaging device when the subject is illuminated with the second light beam among the first, second, and third light beams, and
  a third group of images of the fourth, fifth, and sixth light beams acquired by the imaging device when the subject is illuminated with the third light beam among the first, second, and third light beams.

6. The image forming apparatus according to claim 5,
wherein the one or more objective lenses include
  a first objective lens located in an optical path connecting the subject and the first region,
  a second objective lens located in an optical path connecting the subject and the second region, and
  a third objective lens located in an optical path connecting the subject and the third region.

7. The image forming apparatus according to claim 5, further comprising:
a microlens array located between the one or more objective lenses and the imaging surface,
wherein the one or more objective lenses are a single objective lens that receives a light beam that has passed through the first aperture, a light beam that has passed through the second aperture, and a light beam that has passed through the third aperture.

8. An image forming apparatus, comprising:
a first emitter that emits first light that oscillates in a first plane to an object during a first period, the first plane being parallel to a second plane defined by turning a plane by 30 degrees around a line included in the plane in a first direction;
a second emitter that emits second light that oscillates in a third plane to the object during a second period, the third plane being parallel to a fourth plane defined by turning the plane by 90 degrees around the line in the first direction, the first period not overlapping the second period;
a third emitter that emits third light that oscillates in a fifth plane to the object during a third period, the fifth plane being parallel to a sixth plane defined by turning the plane by 150 degrees around the line in the first direction, the third period not overlapping the first period, the third period not overlapping the second period;
a beam splitter that (i) receives first resulting light and emits first polarized light, second polarized light, and third polarized light, (ii) receives second resulting light and emits fourth polarized light, fifth polarized light, and sixth polarized light, and (iii) receives third resulting light and emits seventh polarized light, eighth polarized light, and ninth polarized light, the object emitting the first resulting light by reflecting the first light, the object emitting the second resulting light by reflecting the second light, the object emitting the third resulting light by reflecting the third light;
an imaging device including first pixels, second pixels, and third pixels; and
an image forming circuit,
wherein each of the first polarized light, the fourth polarized light, and the seventh polarized light oscillates in a seventh plane parallel to the plane,
each of the second polarized light, the fifth polarized light, and the eighth polarized light oscillates in an eighth plane parallel to a ninth plane defined by turning the plane by 60 degrees around the line in the first direction,
each of the third polarized light, the sixth polarized light, and the ninth polarized light oscillates in a tenth plane parallel to an eleventh plane defined by turning the plane by 120 degrees around the line in the first direction,
the first pixels receive the first polarized light and output first pixel values each corresponding to the first pixels, the second pixels receive the second polarized light and output second pixel values each corresponding to the second pixels, the third pixels receive the third polarized light and output third pixel values each corresponding to the third pixels, the first pixels receive the fourth polarized light and output fourth pixel values each corresponding to the first pixels, the second pixels receive the fifth polarized light and output fifth pixel values each corresponding to the second pixels, the third pixels receive the sixth polarized light and output sixth pixel values each corresponding to the third pixels, the first pixels receive the seventh polarized light and output seventh pixel values each corresponding to the first pixels, the second pixels receive the eighth polarized light and output eighth pixel values each corresponding to the second pixels, the third pixels receive the ninth polarized light and output ninth pixel values each corresponding to the third pixels, the image forming circuit calculates pixel values using an equation of $p(i)=[(p1(i)+P2(i)+p5(i)+p6(i)+p7(i)+p9(i))\times(2/3)-(p3(i)+p4(i)+p8(i))/3]$ and generates an image of the object based on the calculated pixel values, and the $p1(i)$, included in the first pixel values, corresponds to the $p2(i)$ included in the second pixel values, the $p3(i)$ included in the third pixel values, the $p4(i)$ included in the fourth pixel values, the $p5(i)$ included in the fifth pixel values, the $p6(i)$ included in the sixth pixel values, the $p7(i)$ included in the seventh pixel values, the $p8(i)$ included in the eighth pixel values, and the $p9(i)$ included in the ninth pixel values, and the i is a natural number.

* * * * *